US012569205B2

(12) United States Patent
Goil et al.

(10) Patent No.: US 12,569,205 B2
(45) Date of Patent: Mar. 10, 2026

(54) IMPLANTABLE MEDICAL DEVICE DATA AND DIAGNOSTICS MANAGEMENT SYSTEM METHOD USING MACHINE-LEARNING ARCHITECTURE

(71) Applicant: Pacesetter, Inc., Sylmar, CA (US)

(72) Inventors: Aditya Goil, Stevenson Ranch, CA (US); Kevin Davis, Thousand Oaks, CA (US); Elnaz Lashgari, Anaheim Hills, CA (US); Gabriel Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 283 days.

(21) Appl. No.: 18/362,582

(22) Filed: Jul. 31, 2023

(65) Prior Publication Data

US 2024/0065637 A1 Feb. 29, 2024

Related U.S. Application Data

(60) Provisional application No. 63/401,515, filed on Aug. 26, 2022.

(51) Int. Cl.
*G16H 10/60* (2018.01)
*A61B 5/00* (2006.01)
(52) U.S. Cl.
CPC ............ *A61B 5/7282* (2013.01); *A61B 5/686* (2013.01); *A61B 5/7221* (2013.01); (Continued)
(58) Field of Classification Search
CPC ....... A61B 5/0006; A61B 5/346; A61B 5/686; A61B 5/7221; A61B 5/7267; (Continued)

(56) References Cited

U.S. PATENT DOCUMENTS

| | | |
|---|---|---|
| 11,562,222 B2 | 1/2023 | Galloway et al. |
| 2005/0115561 A1 | 6/2005 | Stahmann |

(Continued)

OTHER PUBLICATIONS

Office Action dated Mar. 22, 2023, U.S. Appl. No. 17/341,436, filed Jun. 8, 2021.

(Continued)

*Primary Examiner* — George Manuel
(74) *Attorney, Agent, or Firm* — Pearl Cohen Zedek Latzer Baratz LLP

(57) ABSTRACT

A medical data and diagnostics management system for processing classified electrogram (EGM) datasets includes a server system that receives transmissions of classified EGM datasets, each corresponding to an arrhythmic episode detected by an implantable medical device (IMD), and applies a machine-learning model to each classified EGM dataset, thereby determining confidence indicator(s) relating to the IMD classification for each arrhythmic episode. Based upon the confidence indicator(s), the server system generates a set of machine-adjudicated EGM datasets, assigns a ranking score to each machine-adjudicated EGM dataset, and selects for display (for clinical analysis) a subset of the machine-adjudicated EGM datasets based upon their ranking scores. The machine-adjudicated EGM datasets are also stored in a database and further processed to generate diagnostic information and/or diagnostic alerts relating to the arrhythmic episodes detected by the IMD over time. The server system may also facilitate reprogramming of the IMD to improve its performance.

22 Claims, 10 Drawing Sheets

(52) U.S. Cl.
CPC ............ *A61B 5/7267* (2013.01); *A61B 5/742* (2013.01); *A61B 5/746* (2013.01); *G16H 10/60* (2018.01)

(58) Field of Classification Search
CPC ..... A61B 5/7275; A61B 5/7282; A61B 5/742; A61B 5/746; G16H 10/60
See application file for complete search history.

(56) References Cited

U.S. PATENT DOCUMENTS

| | | |
|---|---|---|
| 2008/0300497 A1 | 12/2008 | Krause |
| 2010/0106036 A1 | 4/2010 | Dong |
| 2013/0116578 A1 | 5/2013 | An |
| 2017/0290550 A1 | 10/2017 | Perschbacher |
| 2018/0042510 A1 | 2/2018 | Nakar |
| 2018/0192894 A1 | 7/2018 | An et al. |
| 2019/0336026 A1 | 11/2019 | Dawoud |
| 2020/0008696 A1 | 1/2020 | Sirendi |
| 2020/0178825 A1 | 6/2020 | Lu |
| 2020/0357518 A1* | 11/2020 | Musgrove .............. A61B 5/361 |
| 2021/0020294 A1 | 1/2021 | Bharmi et al. |
| 2021/0345897 A1 | 11/2021 | Moore et al. |
| 2022/0117538 A1 | 4/2022 | Davis et al. |

OTHER PUBLICATIONS

Office Action dated Dec. 15, 2022, U.S. Appl. No. 17/341,436, filed Jun. 8, 2021.
Response to Extended European Search Report dated Jun. 28, 2024, European Patent Application No. 23189024.5.
Extended European Search Report dated Jan. 30, 2024, European Patent Application No. 23189024.5.
Office Action dated Nov. 4, 2025, European Patent Application No. 23189024.5.

* cited by examiner

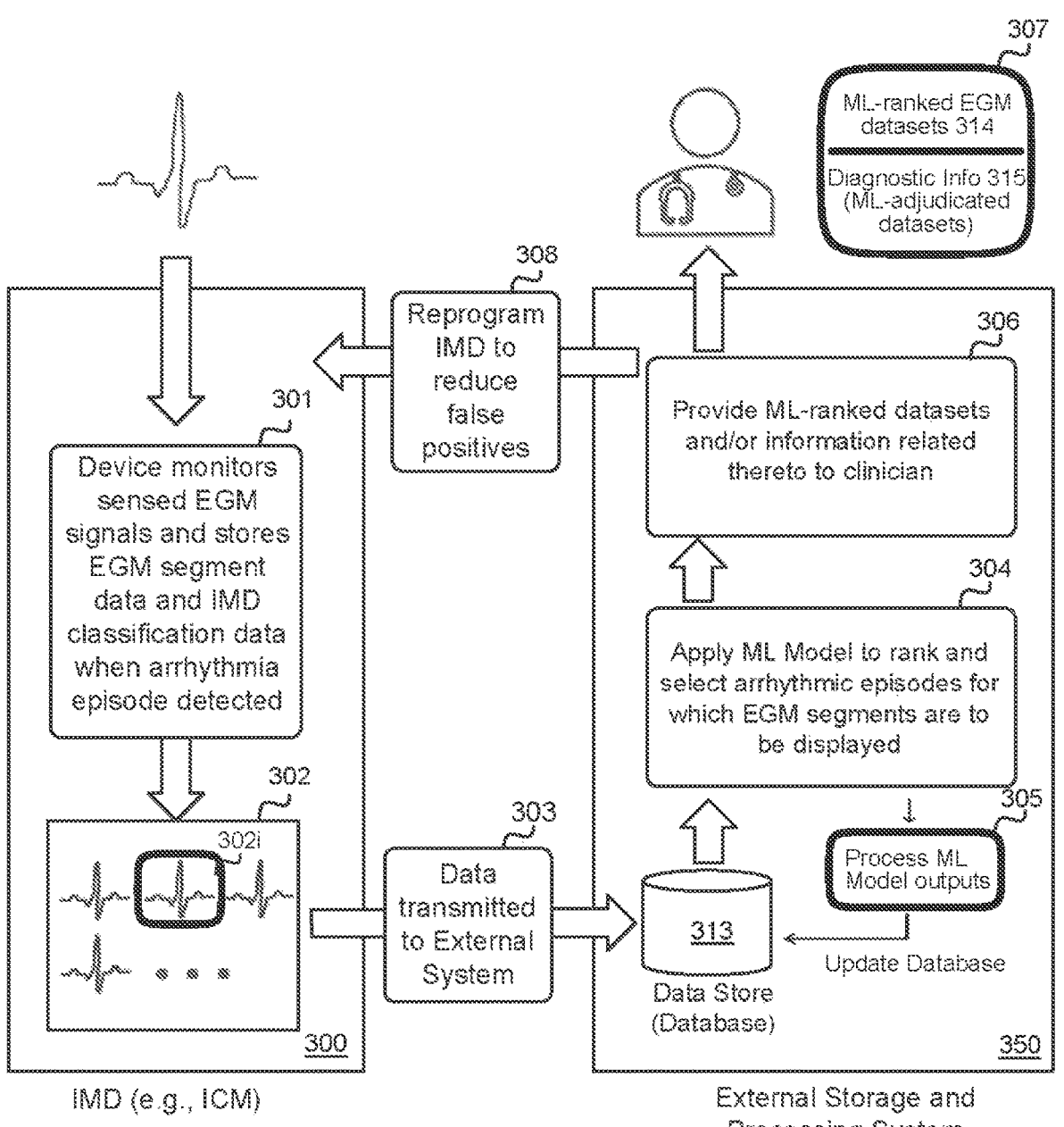

307

ML-ranked EGM
datasets 314

Diagnostic Info 315
(ML-adjudicated
datasets)

308

Reprogram
IMD to
reduce
false
positives

306

Provide ML-ranked datasets
and/or information related
thereto to clinician

301

Device monitors
sensed EGM
signals and stores
EGM segment
data and IMD
classification data
when arrhythmia
episode detected

304

Apply ML Model to rank and
select arrhythmic episodes for
which EGM segments are to
be displayed

302

302i

303

Data
transmitted
to External
System

305

Process ML
Model outputs

313

Data Store
(Database)

Update Database

300

IMD (e.g., ICM)

350

External Storage and
Processing System

FIG. 3A

Classified EGM datasets (302)

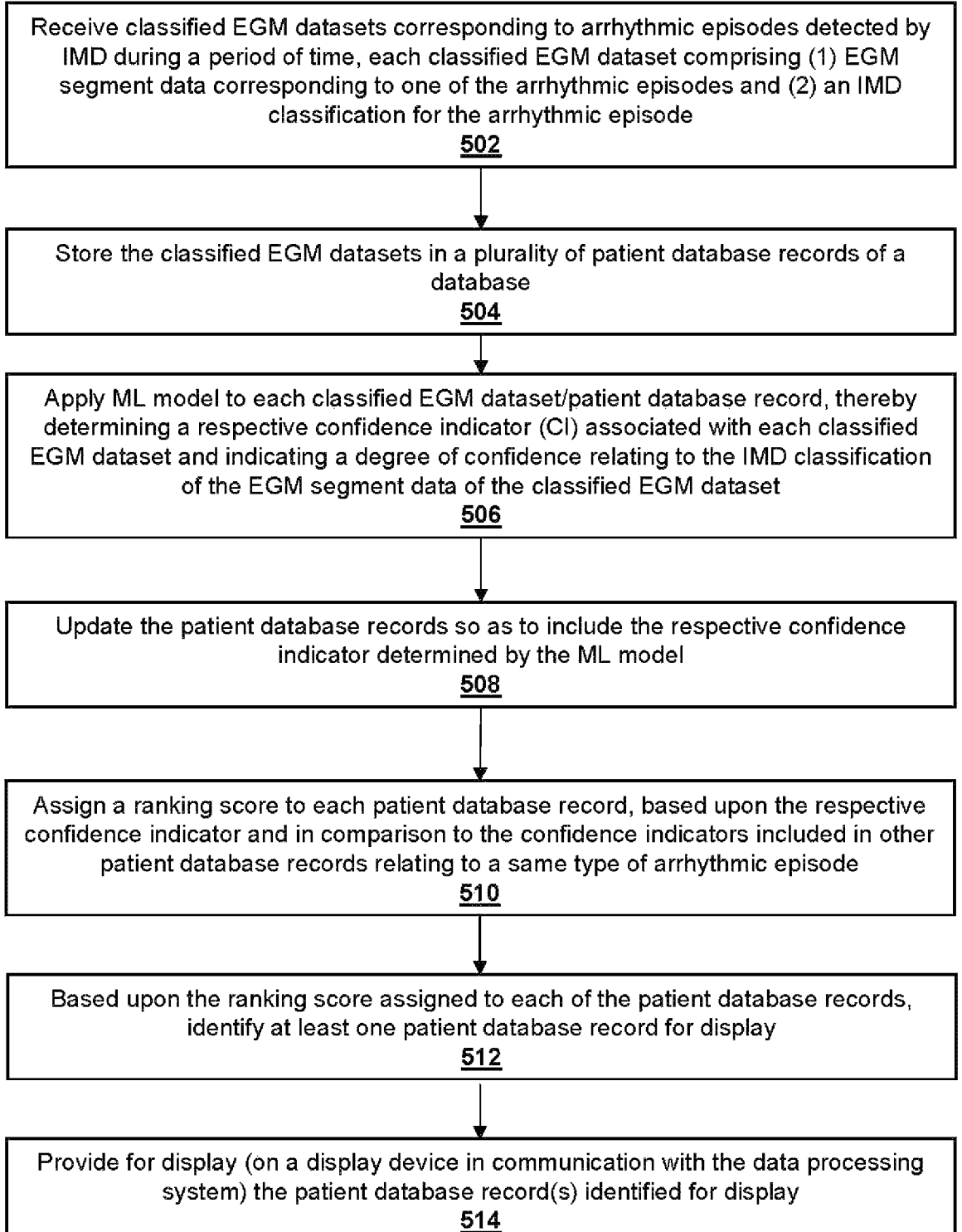

500

Receive classified EGM datasets corresponding to arrhythmic episodes detected by IMD during a period of time, each classified EGM dataset comprising (1) EGM segment data corresponding to one of the arrhythmic episodes and (2) an IMD classification for the arrhythmic episode
502

Store the classified EGM datasets in a plurality of patient database records of a database
504

Apply ML model to each classified EGM dataset/patient database record, thereby determining a respective confidence indicator (CI) associated with each classified EGM dataset and indicating a degree of confidence relating to the IMD classification of the EGM segment data of the classified EGM dataset
506

Update the patient database records so as to include the respective confidence indicator determined by the ML model
508

Assign a ranking score to each patient database record, based upon the respective confidence indicator and in comparison to the confidence indicators included in other patient database records relating to a same type of arrhythmic episode
510

Based upon the ranking score assigned to each of the patient database records, identify at least one patient database record for display
512

Provide for display (on a display device in communication with the data processing system) the patient database record(s) identified for display
514

Figures 7A, 7B:
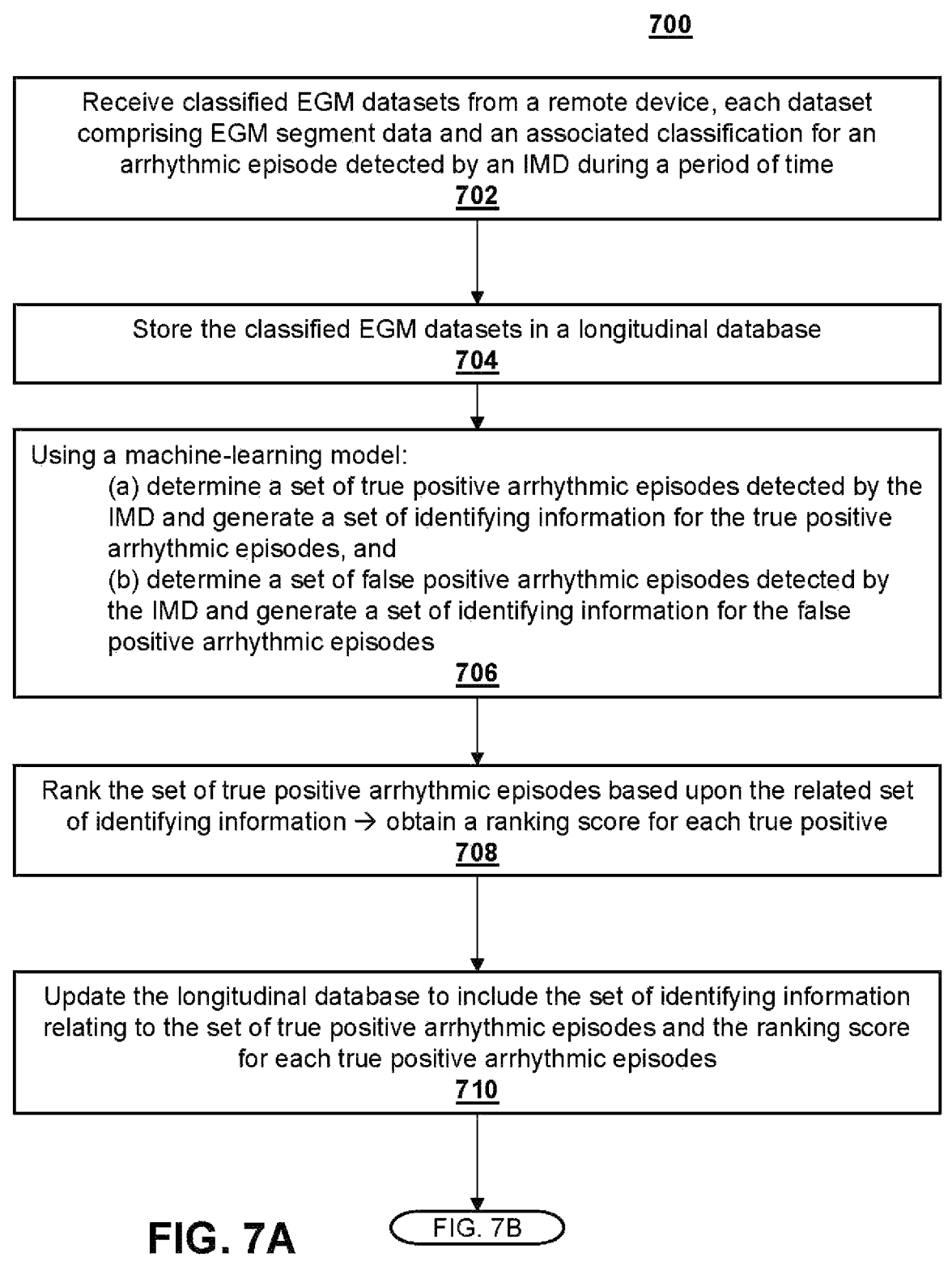

Receive classified EGM datasets from a remote device, each dataset comprising EGM segment data and an associated classification for an arrhythmic episode detected by an IMD during a period of time
702

Store the classified EGM datasets in a longitudinal database
704

Using a machine-learning model:
(a) determine a set of true positive arrhythmic episodes detected by the IMD and generate a set of identifying information for the true positive arrhythmic episodes, and
(b) determine a set of false positive arrhythmic episodes detected by the IMD and generate a set of identifying information for the false positive arrhythmic episodes
706

Rank the set of true positive arrhythmic episodes based upon the related set of identifying information → obtain a ranking score for each true positive
708

Update the longitudinal database to include the set of identifying information relating to the set of true positive arrhythmic episodes and the ranking score for each true positive arrhythmic episodes
710

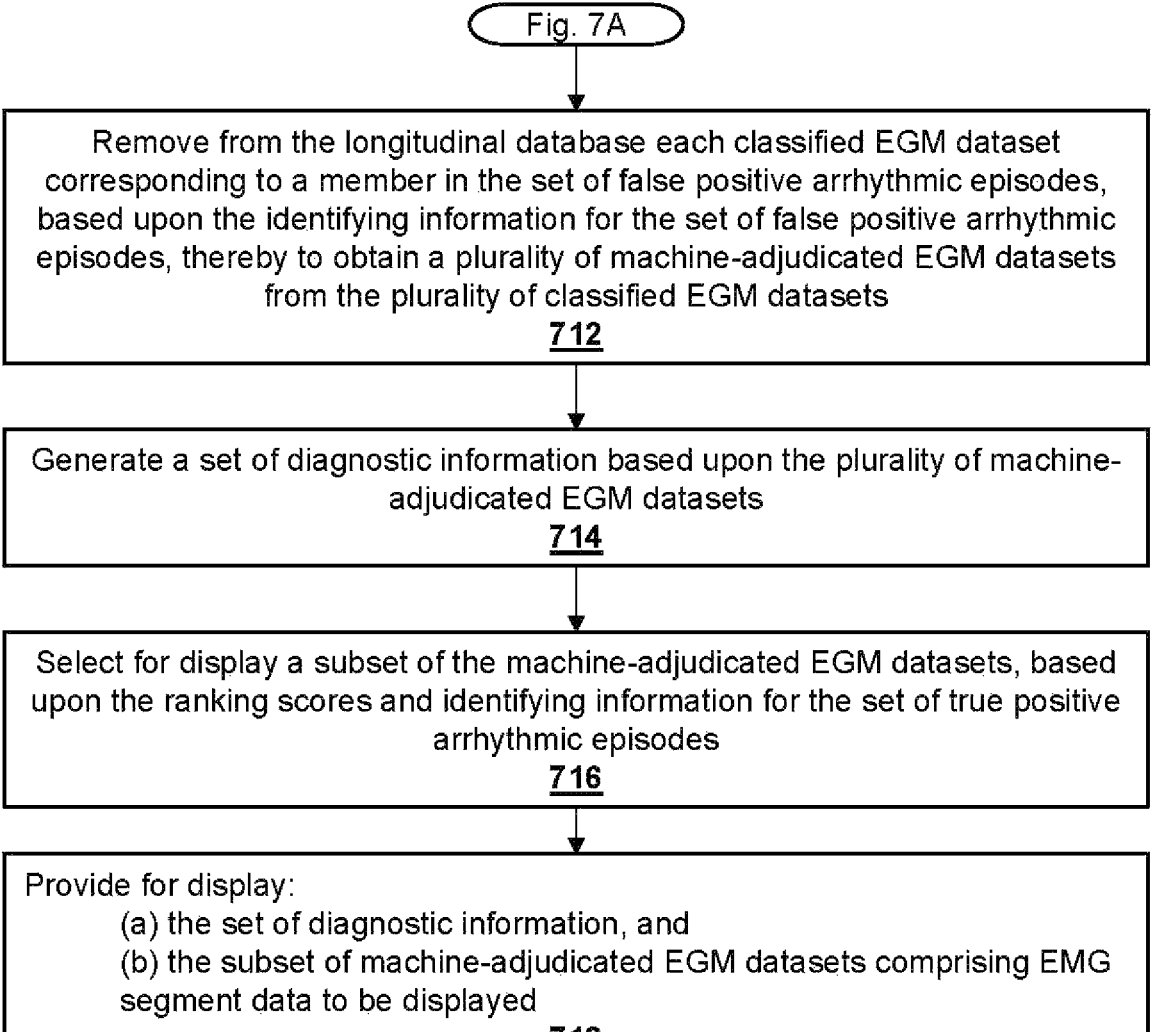

Fig. 7A

Remove from the longitudinal database each classified EGM dataset corresponding to a member in the set of false positive arrhythmic episodes, based upon the identifying information for the set of false positive arrhythmic episodes, thereby to obtain a plurality of machine-adjudicated EGM datasets from the plurality of classified EGM datasets
712

Generate a set of diagnostic information based upon the plurality of machine-adjudicated EGM datasets
714

Select for display a subset of the machine-adjudicated EGM datasets, based upon the ranking scores and identifying information for the set of true positive arrhythmic episodes
716

Provide for display:
    (a) the set of diagnostic information, and
    (b) the subset of machine-adjudicated EGM datasets comprising EMG segment data to be displayed
718

FIG. 7B

IMPLANTABLE MEDICAL DEVICE DATA AND DIAGNOSTICS MANAGEMENT SYSTEM METHOD USING MACHINE-LEARNING ARCHITECTURE

PRIORITY CLAIM

This application claims priority to U.S. Provisional Patent Application No. 63/401,515, titled IMPLANTABLE MEDICAL DEVICE DATA AND DIAGNOSTICS MANAGEMENT SYSTEM AND METHOD USING MACHINE-LEARNING ARCHITECTURE, which was filed Aug. 26, 2022, and which is incorporated herein by reference.

RELATED APPLICATION

The present application is related to U.S. patent application Ser. No. 17/341,436, titled METHODS AND SYSTEMS TO CONFIRM DEVICE CLASSIFIED ARRHYTHMIAS UTILIZING MACHINE LEARNING MODELS, which was filed Jul. 8, 2021, and which is incorporated by reference herein.

TECHNICAL FIELD

Embodiments of the present technology described herein relate generally to systems and methods for processing data obtained from an implantable medical device (IMD) by utilizing machine-learning models to manage presentation of electrogram (EGM) segments corresponding to detected arrhythmic episodes, and to generate and manage clinical diagnostic information associated with such episodes.

BACKGROUND

Implantable Cardiac Monitors (ICMs), which are also known as Insertable Cardiac Monitor (ICM) devices, have become an invaluable tool for ambulatory diagnosis of cardiac arrhythmias, remote monitoring of cardiac arrhythmias, and more generally remote patient care. However, one of the challenges with using such devices is deciding how much data should be available to medical personnel (aka clinicians) to manually review in the form of recorded electrogram (EGM) segments. This is at least in part because timely review and adjudication of the EGM segments corresponding to arrhythmia detections, e.g., to identify clinically actionable arrhythmias, requires significant resources for device monitoring clinics. Initially, the field was receptive to receiving and reviewing every single EGM segment recorded by an ICM device or other type of IMD. However, as ICM devices became smaller in size and their use increased, clinics began to be inundated with data that did not always have clinical value, e.g., due to redundancy and/or false arrhythmia detections. The recent increase in the number of implanted ICM devices with remote monitoring capability, and a corresponding increase in the volume of EGM segments requiring adjudication by a clinician, revealed the need for efficient EGM prioritization tools that do not compromise diagnostic yield. Over time, the consensus among clinics and medical personnel has changed, and depending on the patient type or reason for monitoring and size of the clinic, a preference was adopted to receive less data, despite the potential cost of slight delays in diagnosis.

Existing ICMs are now designed to implement various arrhythmia detection processes to identify clinically actionable arrhythmias. For example, currently available ICMs implement algorithms to detect arrhythmias based on various criteria, such as irregularities and variation patterns in R-wave to R-wave (RR) intervals. In some ICMs, the arrhythmia detection process steps (beat-by-beat) through cardiac activity signals and analyzes the characteristics of interest, such as RR intervals over a period of time. An arrhythmic episode is declared by the IMD based on the characteristics of interest, such as when the RR interval pattern for the suspect beat segments is sufficiently irregular and dissimilar from RR interval patterns for sinus beat segments. When the ICM declares an arrhythmic episode, the ICM stores the cardiac activity signals (e.g., electrocardiograms (ECG) or EGM signals) associated with the episode as an arrhythmic episode (AE) dataset, and includes with that AE dataset one or more device documented (DD) markers and/or other form of signal classifications designating aspects of interest within the cardiac activity signals and/or arrhythmic episode.

Such existing arrhythmic episode detection processes, however, may at times declare arrhythmic episodes when a patient is not in fact experiencing an arrhythmia (a "false positive" or "false arrhythmic episode"). When a false arrhythmic episode is declared, the ICM will nonetheless store the EGM signals associated with the false arrhythmic episode as an AE dataset along with DD markers (albeit incorrect/false DD markers), thereby generating false IMD classifications. Such false arrhythmia detections, and associated false IMD classifications, may arise due to various conditions and behavior of the heart, such as when a patient experiences sick sinus rhythms with irregular RR intervals, or experiences frequent premature ventricular contractions (PVCs) and/or inappropriate R-wave sensing (e.g., R-wave undersensing and/or oversensing). In some instances, false arrhythmia detection is due, in part, to dependence upon identification of R-wave features, with little or no input concerning other features of a cardiac event. PVCs, in general, introduce unstable RR intervals, such as short-long RR intervals, where the instability may give rise to an erroneous ICM declaration of an atrial fibrillation (AF) episode. Thus, PVCs present a substantial challenge in connection with current AF detection algorithms in ICMs that rely on RR interval variability.

Additionally, for certain implantable devices and conditions, large numbers of AE datasets may be stored and transmitted due to frequent false detections. This is particularly a challenge with ICMs, in which computational power is limited and signal fidelity is often degraded. A high number of false arrhythmic episodes places an undue burden on clinicians, who often must spend considerable time manually reviewing or otherwise analyzing the AE datasets. In addition, where AE datasets including EGM segment data and respective IMD classification data obtained by an ICM may be used to generate summary diagnostic information, inclusion of false positives can introduce important inaccuracies in diagnostic histograms and reported trends over time for a given patient, and thus potentially mislead or even obscure an accurate diagnosis, with consequential delay in timely treatment and care.

What is needed, therefore, is a system and method for reducing the burden placed on clinicians in reviewing classified EGM segment data corresponding to EGM signals detected by an IMD and AE datasets uploaded from the IMD, and for mitigating errors and inaccuracies that are introduced into summary diagnostic information for an IMD-implanted patient in connection with erroneous classifications of arrhythmic episodes detected by the IMD.

BRIEF SUMMARY

An implantable medical device data and diagnostics management system and associated methods using machine-learning architecture are described herein. The system includes a server system that receives transmissions of classified EGM datasets, where each classified EGM dataset corresponds to an arrhythmic episode detected by an implantable medical device (IMD) during a period of time, and applies a machine-learning model to each classified EGM dataset, thereby determining one or more confidence indicators relating to the IMD classification for each arrhythmic episode. Based upon the confidence indicator(s), the server system generates a set of machine-adjudicated EGM datasets, assigns a ranking score to each machine-adjudicated EGM dataset, and selects for display (for clinical analysis) a subset of the machine-adjudicated EGM datasets based upon their ranking scores. The machine-adjudicated EGM datasets are also stored in a database and further processed to generate diagnostic information and/or diagnostic alerts relating to the arrhythmic episodes detected by the IMD over time.

In accordance with certain embodiments herein, and as described in further detail below, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by a data processing apparatus, cause the apparatus to perform the actions.

In one embodiment, a method for analyzing data obtained from an IMD is described. The method includes receiving, in a data processing system (such as, for example, a server system comprising one or more servers), a plurality of classified electrogram (EGM) datasets corresponding to a plurality of arrhythmic episodes detected by the IMD during a period of time, where each classified EGM dataset includes (1) EGM segment data corresponding to an arrhythmic episode, and (2) an IMD classification for the arrhythmic episode. In this embodiment, the method further includes: (a) storing the plurality of classified EGM datasets in a plurality of patient database records of a database; (b) applying a machine-learning model to each classified EGM dataset of the plurality of patient database records, where the machine-learning model is configured to determine a respective confidence indicator associated with the classified EGM dataset of a patient database record and is indicative of a degree of confidence relating to the IMD classification and the EGM segment data of the classified EGM dataset; (c) updating the patient database record so as to include the respective confidence indicator determined for and associated with the classified EGM dataset stored in the patient database record; (d) assigning a ranking score to the patient database record based upon the respective confidence indicator included in the patient database record, and in comparison to a set of respective confidence indicators relating to the same type of arrhythmic episode and included in other ones of the patient database records stored in the database; (e) identifying, in the data processing system and based upon the ranking scores assigned to the plurality of patient database records, at least one patient database record for display; and (f) providing for display on a display device in communication with the data processing system, the at least one patient database record identified for display. Other embodiments of this aspect include corresponding computer systems, apparatus, and computer programs recorded on one or more computer storage devices, each configured to perform the actions of the methods.

In some embodiments, the system includes a server, which may comprise one or more computers, a cloud-based server, and/or a virtual server. In some embodiments, the database may include a longitudinal database.

In some embodiments, for each classified EGM dataset, the respective confidence indicator is indicative of a degree of confidence that the IMD classification included in the classified EGM dataset represents a true positive designation of a type of arrhythmic episode corresponding to the EGM segment. In other embodiments, the respective confidence indicator is indicative of a degree of confidence that the IMD classification included in the classified EGM dataset represents a false positive designation of a type of arrhythmic episode corresponding to the EGM segment. Additionally, or alternatively, in some embodiments, a classified EGM dataset is associated with a respective confidence indicator indicative of a degree of confidence in an accuracy of identifying an EGM signal feature of the type of arrhythmic episode. Additionally, or alternatively, in some embodiments, a classified EGM dataset is associated with a respective confidence indicator indicative of a degree of confidence in a sensitivity level utilized by the IMD to identify one or more EGM signal features corresponding to a type of arrhythmic episode. Additionally, or alternatively, in some embodiments, a classified EGM dataset is associated with a respective confidence indicator indicative of a degree of signal noise in the EGM segment data of the classified EGM dataset.

The method may also include determining whether the classified EGM datasets corresponding to arrhythmic episodes detected by the IMD includes a data signal temporal gap, corresponding to missing information. In certain such embodiments, the method may also include: (a) interpolating an approximate EGM dataset suggested by the data signal temporal gap; (b) storing the approximate EGM dataset in the database; and (c) generating diagnostic information from at least one patient database record and the approximate EGM dataset.

In some embodiments, the method may further include determining an alternative classification for one or more said classified EGM dataset stored in the plurality of patient database records for which the respective confidence indicator associated with the classified EGM dataset is indicative of a false positive designation of the type of arrhythmic episode corresponding to the EGM segment data; and modifying one or more said patient database record for which the respective confidence indicator associated with the classified EGM dataset is indicative of a false positive designation of the type of arrhythmic episode by replacing the IMD classification with the alternative classification and by updating the respective confidence indicator to an alternative confidence indicator, thereby associating a different type of arrhythmic episode with the EGM segment data of the classified EGM dataset stored in the patient database record.

In some embodiments, the method may include facilitating a reprogramming of a set of instructions stored in the IMD in response to a plurality of said respective confidence indicators indicating a threshold level alert for at least one type of arrhythmic episode of the plurality of arrhythmic episodes detected by the IMD during the period of time. For example, one alert may be triggered by a threshold level of false positives of at least one type of arrhythmic episode (e.g., too many) being exceeded; another alert may be triggered by a threshold level of true positives of at least one type of arrhythmic episode (e.g., too few) not being reached. In some embodiments, the method also may include: (a) removing one or more patient database record from the database for which the respective confidence indicator included in the patient database record is indicative of a false positive designation of the type of arrhythmic episode corresponding to the EGM segment data of the patient database record, thereby creating a plurality of machine-adjudicated patient database records stored in the database; (b) generating diagnostic information from at least some of the machine-adjudicated patient database records; and (c) providing for display on the display device the diagnostic information. In some such embodiments, the generating diagnostic information includes associating a diagnostic alert with at least one type of arrhythmic episode represented in the plurality of arrhythmic episodes, based upon one or more confidence indicators of a plurality of respective confidence indicators, wherein associating the diagnostic alert with the at least one type of arrhythmic episode is further based upon the set of diagnostic information.

Implementations of the above-described techniques may include hardware, a method or process, or computer software on a computer-accessible medium.

A data processing system for analyzing a dataset associated with EGM data is also described. In one embodiment, the data processing system includes an IMD configured to detect, record and transmit a plurality of signals corresponding to one or more classified EGM datasets representing a set of arrhythmic episodes, and an external device configured to receive and re-transmit the plurality of signals to a server system via a communication link. In this embodiment, the server system may include one or more server processors, a database, a server memory, and a network interface. The server system may be cloud-based. As described below, the server system may be configured to: (a) store and execute a machine-learning model that determines at least one confidence indicator relating to each classified EGM dataset and generates, for each classified EGM dataset, a machine-adjudicated EGM dataset including said confidence indicator(s); (b) generate a set of diagnostic information based upon the machine-adjudicated EGM datasets; and (c) select for display (on, for example, a clinician's display device) one or more machine-adjudicated EGM datasets from a plurality of said machine-adjudicated EGM datasets. The server system may be further be configured to store the machine-adjudicated EGM datasets in relation to the set of arrhythmic episodes and the set of diagnostic information in a longitudinal database for additional processing, including for generating diagnostic alerts for clinical purposes. Embodiments of this aspect include corresponding computer systems, apparatus, and computer programs recorded on one or more computer storage devices, each configured to perform the actions of the methods described herein.

Implementations of the above may further include one or more of the following features: (a) the server system is a cloud-based system, and the communication link is a wireless communication link; (b) the IMD is further configured to transmit an alert signifying a request to initiate transmission of the plurality of signals to the external device; (c) a set of instructions is configured to identify a temporal gap in the plurality of classified EGM datasets, interpolate an approximate EGM dataset suggested by the plurality of classified EGM datasets, and update a data storage to include the approximate EGM dataset in the plurality of classified EGM datasets so as to eliminate the temporal gap. In some embodiments, the data storage is a component of the database. In some embodiments, the database is a longitudinal database. Implementations of the described techniques may include hardware, a method or process, or computer software on a computer-accessible medium.

In some embodiments, the system is more specifically configured to: (a) receive, from a remote device, a plurality of classified EGM datasets, wherein each classified EGM dataset includes EGM segment data and an associated classification, and wherein the EGM segment data represents an arrhythmic episode detected by an IMD during a period of time; (b) store, in a longitudinal database, the plurality of classified EGM datasets; (c) process the plurality of classified EGM datasets using a machine-learning model to (1) determine a set of true positive arrhythmic episodes detected by the IMD and generate a first set of identifying information (such as, e.g., confidence indicators, date/time stamps, and/or DD markers) relating to the set of true positive arrhythmic episodes, and (2) determine a set of false positive arrhythmic episodes detected by the IMD and generate a second set of identifying information relating to the set of false positive arrhythmic episodes; (d) rank the set of true positive arrhythmic episodes based upon the first set of identifying information, to obtain a ranking score for each classified EGM dataset corresponding to a true positive arrhythmic episode; (e) update the longitudinal database to include the identifying information and ranking score for each classified EGM dataset corresponding to a true positive arrhythmic episode; (f) remove, from the longitudinal database, each classified EGM dataset from the plurality of classified EGM datasets corresponding to a false positive arrhythmic episodes, based upon the second set of identifying information relating to the set of false positive arrhythmic episodes, thereby obtaining a plurality of machine-adjudicated EGM datasets from the plurality of classified EGM datasets; (g) generate a set of diagnostic information based upon the plurality of machine-adjudicated EGM datasets; (h) select for display a subset of the machine-adjudicated EGM datasets, based upon the ranking scores and identifying information relating to true positive arrhythmic episode(s); and (g) provide for display (on a display device in communication with the system) the set of diagnostic information and the subset of machine-adjudicated EGM datasets, comprising EGM segment data to be displayed. Other embodiments of this aspect include corresponding computer systems, apparatus, and computer programs recorded on one or more computer storage devices, each configured to perform the actions of the methods described herein.

In some embodiments, identifying information relating to the set of false positive arrhythmic episodes may be used to remotely program the IMD. In some embodiments, identifying information relating to the set of true positives may be so used.

In some embodiments, the system is further configured to generate a query to obtain (for example, from a clinician) a set of patient-specific parameter settings configured to (a) enable the machine-learning model to process a set of patient-specific longitudinal data relating to the set of arrhythmic episodes, and (b) select the set of diagnostic information and a set of display criteria associated with the subset of machine-adjudicated EGM datasets to be displayed. In some embodiments, the system is further configured to (a) generate a second query to obtain a set of alert conditions relating to the set of arrhythmic episodes and the patient-specific longitudinal data, (b) generate at least one assessment of an alert condition of the set of alert conditions based upon the set of diagnostic information, and (c) conditionally reset the set of alert conditions based upon the at least one assessment. In some embodiments, the set of patient-specific parameters settings includes a configurable time period used to generate the set of diagnostic information. Implementations of the described techniques may include hardware, a method or process, or computer software on a computer-accessible medium.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

FIGS. 3A and 3B illustrate high-level overviews of systems and methods for processing data obtained from an IMD in accordance with certain embodiments described herein.

FIG. 5 illustrates a process for analyzing data obtained from an IMD in accordance with certain embodiments described herein.

FIGS. 7A and 7B collectively illustrate a process for analyzing data obtained from an IMD, and for managing the clinical presentation of such data, in accordance with certain embodiments described herein.

DETAILED DESCRIPTION

Figure 1:
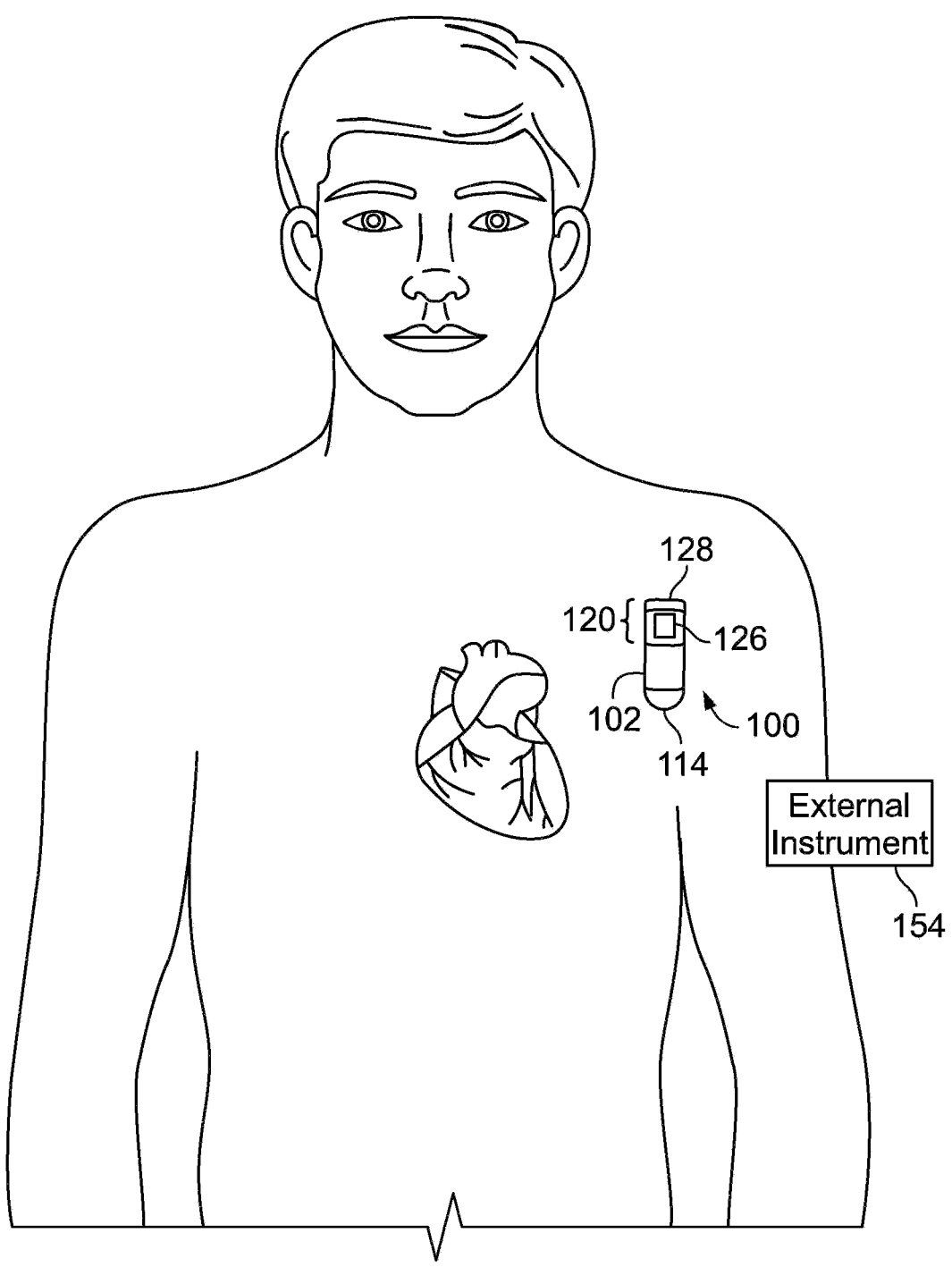
FIG. 1 illustrates one example of an IMD that may be used in some embodiments of the system described herein, and more specifically, illustrates one example of an ICM intended for subcutaneous implantation at a site near the heart.

The IMD data and diagnostics management systems and methods using machine-learning architecture of the present disclosure will now be discussed with respect to embodiments in which the IMD is an ICM, for illustrative purposes only.

In a normal heart, cells of the sinoatrial node (SA node) spontaneously depolarize and thereby initiate an action potential. This action potential propagates rapidly through the atria (which contract), slowly through the atrioventricular node (AV node), the atrioventricular bundle (AV bundle or His bundle) and then to the ventricles, which causes ventricular contraction. This sequence of events is known as normal sinus rhythm (NSR). Thus, in a normal heart, ventricular rhythm relies on conduction of action potentials through the AV node and AV bundle.

Rhythms that do not follow the sequence of events described above are known as arrhythmias. Those that result in a heart rate slower than normal are known as bradyarrhythmias or bradycardias. Those that result in a faster heart rate than normal are called tachyarrhythmias or tachycardias. Tachyarrhythmias (aka tachycardias) are further classified as supraventricular tachycardias (SVTs) and ventricular tachycardias (VTs). VTs are heart rhythm disorders (arrhythmias) caused by abnormal electrical signals in the ventricles, which are the lower chambers of the heart. SVTs, by contrast, are generally characterized by abnormal heart rhythms that arise in the atria, which are the upper chambers of the heart, or the atrioventricular node (AV node). Additionally, there are various different types of SVTs and various different types of VTs that can be characterized. For example, a paroxysmal SVT can exhibit heart rates between approximately 140 beats per minute (bpm) and approximately 250 bpm. However, the most common SVTs are typically atrial flutter (AFL) and atrial fibrillation (AF). In addition, many SVTs involve the AV node, for example, AV nodal reentry tachycardia (AVNRT) where an electrical loop or circuit includes the AV node. Another type of SVT is an AV reentrant tachycardia (AVRT), where an AV reentrant circuit typically involves the AV node and an aberrant conducting bundle known as an accessory pathway that connects a ventricle to an atrium.

Atrial flutter (AFL) can result when an early beat triggers a "circus circular current" that travels in regular cycles around the atrium, pushing the atrial rate up to approximately 250 bpm to approximately 350 bpm. The atrioventricular node between the atria and ventricles will often block one of every two beats, keeping the ventricular rate at about 125 bpm to about 175 bpm. This is the pulse rate that will be felt, even though the atria are beating more rapidly. At this pace, the ventricles will usually continue to pump blood relatively effectively for many hours or even days. A patient with underlying heart disease, however, may experience chest pain, faintness, or even heart failure (HF) as a result of the continuing increased stress on the heart muscle. In some individuals, the ventricular rate may also be slower if there is increased block of impulses in the AV node, or faster if there is little or no block.

If the cardiac impulse fails to follow a regular circuit and divides along multiple pathways, a chaos of uncoordinated beats results, producing atrial fibrillation (AF). AF commonly occurs when the atrium is enlarged (usually because of heart disease). In addition, it can occur in the absence of any apparent heart disease. In AF, the atrial rate can increase to more than 350 bpm and cause the atria to fail to pump blood effectively. Under such circumstances, the ventricular beat may also become haphazard, producing a rapid irregular pulse. Although AF may cause the heart to lose approximately 20 to 30 percent of its pumping effectiveness, the volume of blood pumped by the ventricles usually remains within the margin of safety, again because the atrioventricular node blocks out many of the chaotic beats. Hence, during AF, the ventricles may contract at a lesser rate than the atria, for example, of approximately 125 bpm to approximately 175 bpm.

Overall, SVTs are not typically immediately life threatening when compared to ventricular arrhythmias, examples of which are discussed below.

Ventricular arrhythmias, which originate in the ventricles, include ventricular tachycardia (VT) and ventricular fibrillation (VF). Ventricular arrhythmias are often associated with rapid and/or chaotic ventricular rhythms. For example, sustained VT can lead to VF. In sustained VT, consecutive impulses arise from the ventricles at a rate of 100 bpm or more. Such activity may degenerate further into disorganized electrical activity known as VF. In VF, disorganized action potentials can cause the myocardium to quiver rather than contract. Such chaotic quivering can greatly reduce the heart's pumping ability. Indeed, approximately two-thirds of all deaths from arrhythmia are caused by VF. A variety of conditions such as, but not limited to, hypoxia, ischemia, pharmacologic therapy (e.g., sympathomimetics), and asynchronous pacing may promote onset of ventricular arrhythmia. Further, there are various different types of VT, including, e.g., monomorphic VT and polymorphic VT, for which different types of therapy may be appropriate.

Cardiac pause, also known as asystole, refers to a delay between ventricular contractions (identified by R-waves in an EGM) which exceeds a specified time threshold, e.g., 3 seconds. Cardiac pause may coincide with syncope, also known as fainting, which is a temporary loss of consciousness. For example, if an R-R interval exceeds a time threshold (e.g., 3 seconds), a cardiac pause may have occurred, which may be the underlying cause of syncope for a patient. Pacing therapy is one type of treatment that can be used to reduce and preferably prevent cardiac pauses.

Since their inception, ICMs have quickly been established as an invaluable tool for ambulatory diagnosis of various types of cardiac arrhythmias, such as AF, tachycardias, bradycardia, and asystole. However, as noted above, one of the challenges with using such devices is deciding how much data should be made available to medical personnel (aka clinicians) to review in the form of recorded EGM segments. Certain embodiments of the present technology, which are described below, can be used to reduce clinical review burden by managing presentation of EGM segments that correspond to detected arrhythmic episodes, and by improving arrhythmia detections and classifications. Managing the presentation of EGM segments, as will be described below, can involve ranking (aka prioritizing) EGM segments and selecting a subset of the obtained EGM segments (e.g., the highest ranking or prioritized) EGM segments to display to medical personnel, which reduces clinical burden by reducing how many EGM segments are manually reviewed by the medical personnel. Improving arrhythmia detections and classifications can also reduce clinical burden, for example, by reducing the number of false positives manually reviewed by the medical personnel and/or erroneously incorporated into summary diagnostic information for an IMD-implanted patient from EGM segment data recorded by the IMD over a period of time.

The systems and methods described herein manage IMD data and diagnostics using machine-learning (ML) models and architecture that may be configured to achieve multiple such approaches to reducing clinical burden, such as ranking (prioritizing) EGM segments and selecting subsets for display based upon ranking, improving arrhythmia classifications, and improving IMD detection/performance (e.g., sensitivity and/or accuracy).

Prior to providing details of the specific embodiments of the present technology, an example system with which embodiments of the present technology can be used will first be described with reference to FIGS. 1 and 2, which illustrate an ICM monitoring, detection, recording and classification system for cardiac patients and their clinicians. However, it should be noted that embodiments of the present technology are not limited to use with the ICM described below, and in fact, are not limited to use with ICMs. Rather, embodiments of the present technology, as will be explained in further detail below, can be used with various other types of IMDs besides ICMs, such as, but not limited to, implantable pacemakers and implantable cardioverter defibrillators (ICDs). Pacemakers can be conventional pacemakers that include one or more leads that are used for sensing and/or pacing in one or more cardiac chambers, or can be leadless pacemakers. Pacemakers and defibrillators may also include IMDs intended to regulate rhythmic contractions of non-heart tissue. ICDs can include transvenous ICDs and subcutaneous ICDs (S-ICDs).

For most of the following description, embodiments of the present technology will be described as being used with an ICM-type of IMD. However, as just explained above, embodiments of the present technology can also be used with other types of IMDs, examples of which were mentioned above.

FIG. 1 illustrates an example ICM 100 intended for subcutaneous implantation at a site near the heart of a patient. The ICM 100 includes a pair of spaced-apart sense electrodes 114, 126 positioned with respect to a housing 102. The sense electrodes 114, 126 provide for detection of far field EGM signals. Numerous configurations of electrode arrangements are possible. For example, the electrode 114 may be located on a distal end of ICM 100, while the electrode 126 is located on a proximal side of ICM 100. Additionally or alternatively, the electrodes 114, 126 may be located on opposite sides of ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as a header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the arrhythmia detection algorithms, a loop memory for temporary storage of EGM data, a device memory for long-term storage of EGM data upon certain triggering events, such as an arrhythmia detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The ICM 100 may be configured to be activated by the patient or automatically activated, in connection with recording EGM signals.

The ICM 100 senses an EGM signal, processes the EGM signal to detect arrhythmias and, if an arrhythmia is detected, automatically records one or more portions of the EGM signal corresponding to an arrhythmic episode in its memory for subsequent transmission to an external device (as further described below). The EGM signal processing and arrhythmia detection is provided for, at least in part, by algorithms embodied in or implemented by a microprocessor of the ICM 100 (as further described below).

Thus, the ICM 100 includes one or more processors and memory that stores program instructions directing the processor(s) to implement arrhythmia detections utilizing on-board processes that analyze cardiac activity signals (e.g., EGM signals) collected over one or more sensing channels over a period of time. As described in further detail below, the ICM 100 is further configured to manage its memory store and to generate classified EGM datasets for later transmission to an external device (e.g., 154) and/or later download to a remote server system (such as a secured, cloud-based system) for additional processing and clinical evaluation.

Figure 2:
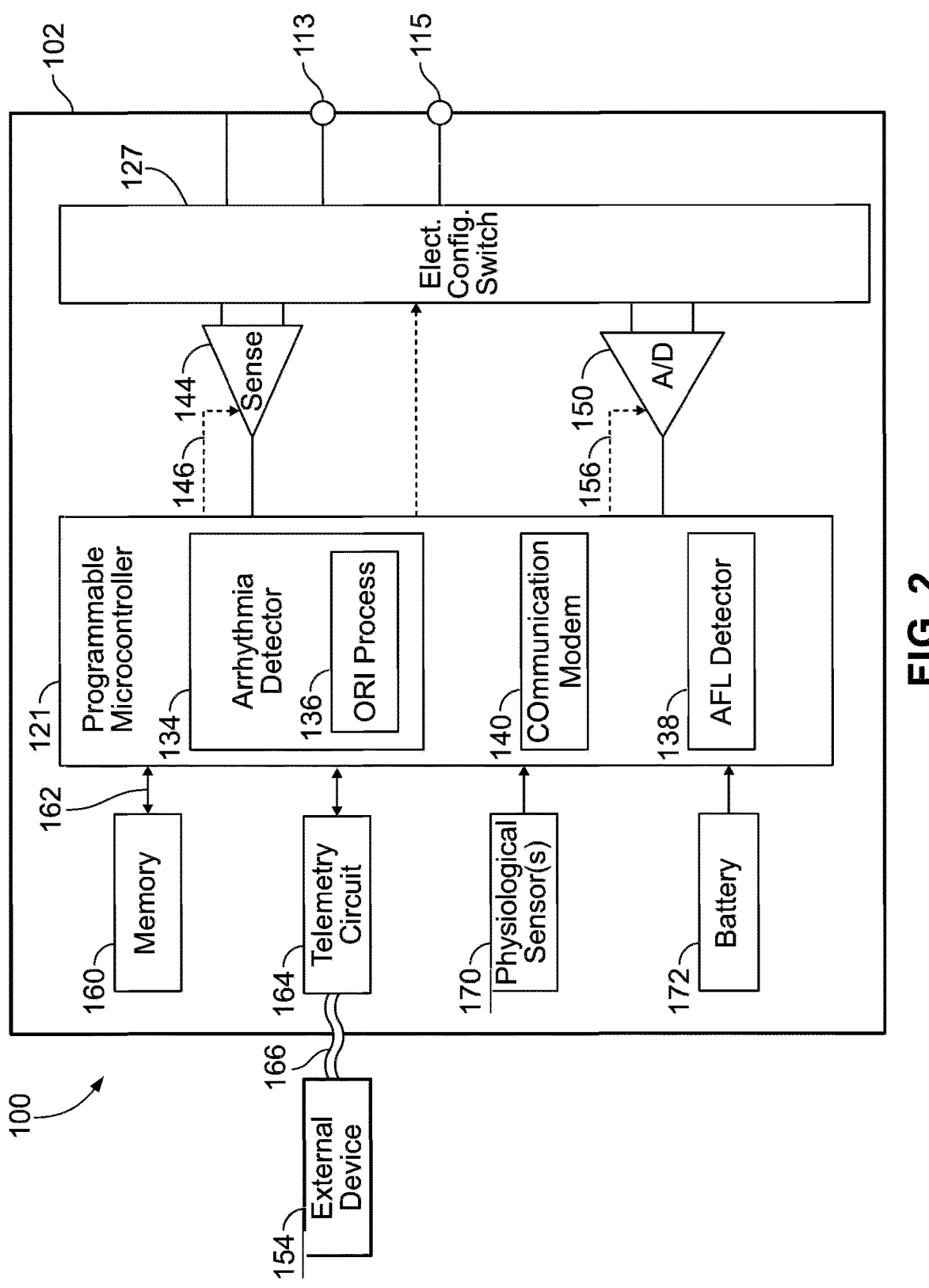
FIG. 2 shows an example block diagram for the IMD introduced in FIG. 1, in accordance with an embodiment of the system described herein.

FIG. 2 shows a block diagram of the example IMD of FIG. 1 (i.e., ICM 100) that may be used in accordance with embodiments of the system and methods described herein. Referring to FIG. 2, the ICM 100 may be implemented to monitor ventricular activity alone, or both ventricular and atrial activity through a sensing circuit 144. As shown in this embodiment, the ICM 100 has a housing 102 to hold electronic/computing components. The housing 102 (which is often referred to as the "can", "case", "encasing", or "case electrode") may be programmably selected to act as an electrode for certain sensing modes. The housing 102 further includes a connector (not shown) with at least one terminal 113 and optionally additional terminals 115. The terminals 113, 115 may be coupled to sensing electrodes (not shown) that are provided upon or immediately adjacent the housing 102. For example, the terminals 113, 115 can be coupled to the electrodes 114, 126 shown in and described above with reference to FIG. 1, but are not limited thereto. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

As shown in FIG. 2, the ICM 100 includes a programmable microcontroller 121 that controls various operations of the ICM 100, including cardiac monitoring. The microcontroller 121 can include, for example, a microprocessor (or equivalent control circuitry), RAM and/or ROM memory, logic and timing circuitry, state machine circuitry, and/or I/O circuitry. The microcontroller 121 can perform the operations described herein in connection with collecting cardiac activity data (e.g., collecting EGM datasets) and analyzing the cardiac activity data (e.g., analyzing EGM datasets).

A switch 127 of the ICM 100 is optionally provided to allow selection of different electrode configurations under the control of the microcontroller 121. The electrode configuration of switch 127 may include multiple switches for connecting desired electrodes to appropriate I/O circuits, thereby facilitating electrode programmability. For example, the switches can be used to connect specific terminals, and the electrodes connected thereto, to inputs of the sensing circuit 144 and/or to inputs of the A/D 150. The switch 127 can be controlled by one or more control signals from the microcontroller 121. Optionally, the switch 127 may be omitted and I/O circuits may be directly connected to the housing electrode 114 and a second electrode 126.

As shown in FIG. 2, the microcontroller 121 includes an arrhythmia detector 134 that is configured to analyze cardiac activity signals (e.g., EGM signals) to identify potential arrhythmic episodes (e.g., tachycardias, bradycardias, cardia pause, AF, etc.). By way of example, the arrhythmia detector 134 may implement an arrhythmia detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and potentially managing pacing therapies (if the IMD 100 is able to perform therapy). The arrhythmia detector 134 of the microcontroller 121 includes one or more on-board arrhythmia detection processes that detects arrhythmic episodes, such as AF episodes using R-R interval irregularities. The arrhythmia detector 124 may be implemented using firmware, software and/or hardware circuits.

The arrhythmia detector 134 analyzes one or more EGM signals sensed using electrodes in order to detect arrhythmic episodes, which can also be referred to interchangeably as an arrhythmic episode or an episode of an arrhythmia. More specifically, where an IMD is an ICM that senses a far field EGM signal, the ICM can analyze a sensed far field EGM signal sensed along a sensing vector between a combination of electrodes for one or more beats. The arrhythmia detector 134 identifies one or more features of interest from the EGM signal(s) and, based on further analysis of the features of interest, determines whether the EGM signal(s) are indicative of a normal sinus rhythm (NSR) or an arrhythmic episode. When an arrhythmic episode is identified, the arrhythmia detector 134 can generate one or more markers that are temporally aligned with corresponding features of interest in the EGM signal(s), or more specifically, segments thereof. Such markers refer to data and/or information identified from EGM signal(s) that may be presented as graphical and/or numeric indicia indicative of one or more features within the EGM signal(s) and/or indicative of one or more episodes exhibited by the cardiac events. Markers may be superimposed upon EGM signals or presented proximate to, and temporally aligned with, EGM signals or segments thereof. Non-limiting examples of markers may include R-wave markers, noise markers, activity markers, interval markers, refractory markers, P-wave markers, T-wave markers, PVC markers, sinus rhythm markers, AF markers and other arrhythmia markers. As further nonlimiting examples, basic event markers may include "AF entry" to indicate a beginning of an AF event, "in AF" to indicate that AF is ongoing, "AF exit" to indicate that AF has terminated, "T" to indicate a tachycardia beat, "B" to indicate a bradycardia beat, "A" to indicate an asystole beat, "VS" to indicate a regular sinus beat, "Tachy" to indicate a tachycardia episode, "Brady" to indicate a Bradycardia episode, "Asystole" to indicate an asystole episode, "Patient activated" to indicate a patient activated episode. An activity marker may indicate activity detected by an activity sensor (e.g., accelerometer) during the EGM signal. Noise markers may be used to indicate entry (aka start), ongoing, recovery and exit (aka stop) of noise. Markers may be presented as symbols, dashed lines, numeric values, thickened portions of a waveform, and the like. Markers may represent events, intervals, refractory periods, ICM activity, and other algorithm related activity. For example, interval markers, such as an R-R interval marker, may include a numeric value indicating the duration of the interval. The AF markers indicate atrial fibrillation rhythmic.

In accordance with certain embodiments of the system and method described herein, in response to the arrhythmia detector 134 detecting and classifying an arrhythmia, the arrhythmia detector 134 (or more generally, the IMD) forms a classified EGM dataset corresponding to an arrhythmic episode and stores the classified EGM dataset in the memory 160 of the IMD. The classified EGM dataset for an arrhythmic episode can include respective EGM segment data and respective IMD classification data for the arrhythmic episode. The respective EGM segment data can be indicative of an EGM segment corresponding to the arrhythmic episode, and may be used to reconstruct the EGM segment for display after the EGM segment data has been uploaded from the IMD to a non-implanted device or system. The respective IMD classification data can specify the type of the arrhythmic episode, as classified by, e.g., ICM 100.

Obtaining EGM Segment Data & IMD Classification Data

Classified EGM datasets, including (without limitation) EGM segment data and associated IMD classifications, can be obtained using a variety of methods, one of which is now described with respect to an ICM. In the discussion which follows, the terms "obtain" and "obtaining", as used in connection with data, signals, information and the like, includes at least one of i) accessing memory of an IMD, ICM, external device or remote server where the EGM data, signals, information, etc. are stored, ii) receiving the data, signals, information, etc. over a wireless communication link between the ICM or other type of IMD and a local external device, iii) receiving the data, signals, information, etc. at a remote server over a network connection and/or iv) sensing signals (e.g., EGM signals, impedance signals, etc.) between a combination of electrodes provided on or coupled to the ICM or other type of IMD. An obtaining operation, when from the perspective of an ICM or other type of IMD, may include sensing new signals in real time, and/or accessing memory to read stored data, signals, information, etc., from the memory (e.g., 160) within the ICM or other type of IMD. The obtaining operation, when from the perspective of a local external device, includes receiving the data, signals, information, etc., at a transceiver of the local external device where the data, signals, information, etc., are transmitted from an ICM and/or a remote server. The obtaining operation may be from the perspective of a remote server, such as when receiving the data, signals, information, etc., at a network interface from a local external device and/or directly from an ICM or other type of IMD. The remote server may also obtain the data, signals, information, etc., from local memory and/or from other memory, such as within a cloud storage environment and/or from the memory of a workstation or clinician external programmer.

Figure 3B:
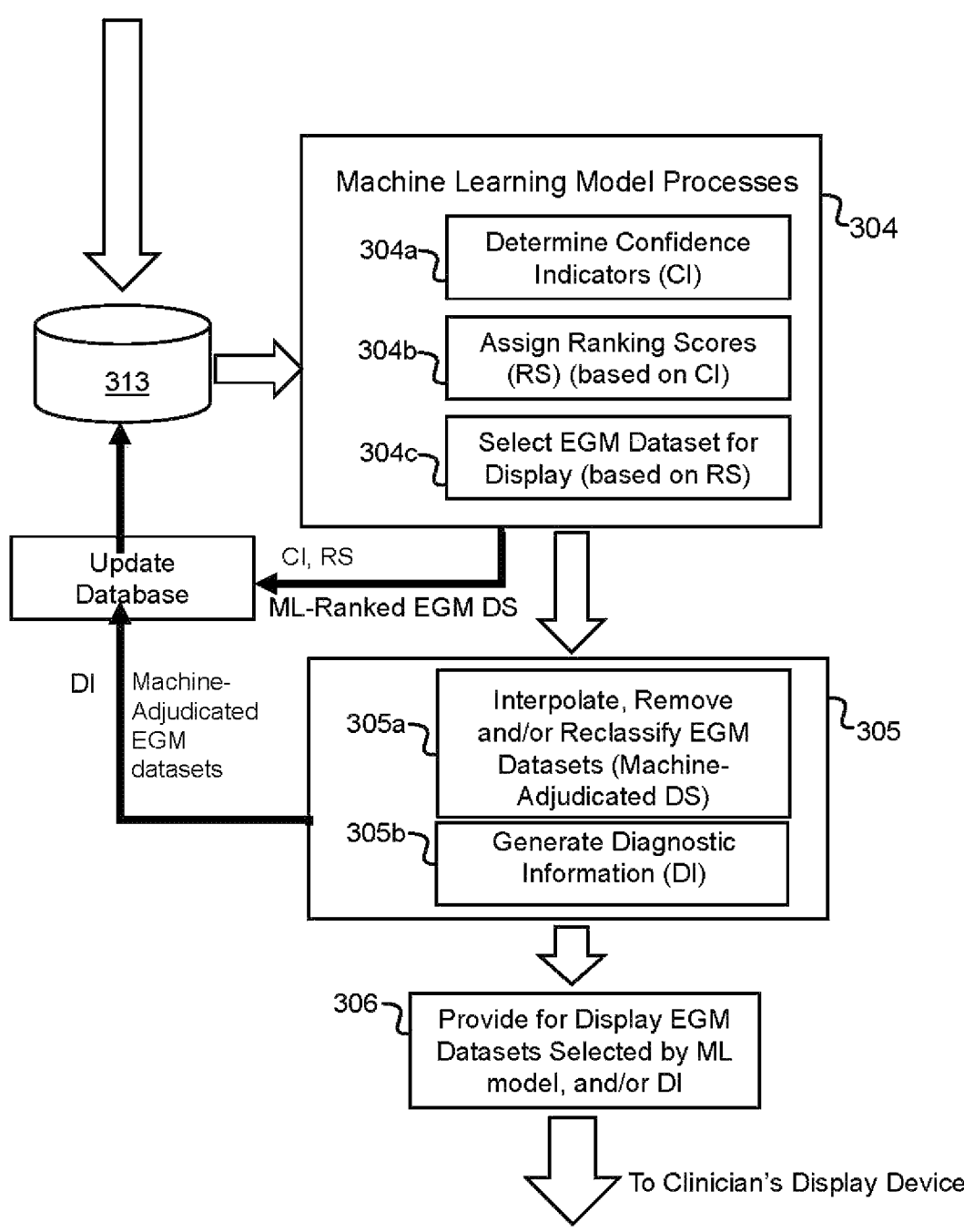

Obtaining respective EGM segment data and respective classification data for each arrhythmic episode of a plurality of arrhythmic episodes detected by the IMD during a period of time will now be described. The respective EGM segment data is indicative of an EGM segment corresponding to the arrhythmic episode; respective classification data specifies a type of the arrhythmic episode, such as, but not limited to, bradycardia, tachycardia, cardiac pause, and AF, as mentioned above. EGM segment data can include temporal information, morphological information and/or frequency information about the EGM segment, which information enables the EGM segment to be reproduced for display to medical personal, and enables the EGM segment to be analyzed, e.g., for the purpose of ranking the arrhythmia episode corresponding to the EGM segment (as further described below and as illustrated in FIGS. 3A and 3B), determining whether the arrhythmia detection was a true positive or a false positive detection, determining whether the arrhythmia episode should be reclassified is being a different type of arrhythmia than originally classified, and/or the like. The respective classification data specifies a type of the arrhythmic episode. The EGM segment data and associated classification data can be obtained directly from an IMD (e.g., ICM 100) that stored such data in its memory (e.g., 160). Alternatively, the EGM segment data and the associated classification data can be obtained from an external device (e.g., 154) that had already obtained such data from an IMD. As described above, a classified EGM dataset includes EGM segment data (which may also include marker data, examples of which were discussed above), associated classification data, and other types of metadata (e.g., a date/time stamp; IMD/patient identifying information; etc.).

By way of example, the ICM 100 may classify a detected arrhythmic episode by obtaining a representative R-R interval, and/or a representative heart rate (HR), for each of the arrhythmic episodes detected. This may involve obtaining a respective duration for each of the arrhythmic episodes detected. In certain embodiments, the manner for determining the representative R-R interval and/or the representative HR for an arrhythmic episode depends on the type of the arrhythmic episode, such that for at least two of the different types of arrhythmic episodes the manners for determining the representative R-R interval or the representative HR differ from one another. Specific manners for determining a representative R-R interval or a representative HR for each of a plurality of different types of arrhythmic episodes, are described below.

More specifically, in this example, the IMD may maintain an episode diagnostic log that records, for each detected arrhythmic episode, the type of arrhythmic episode (e.g., bradycardia, tachycardia, cardiac pause, or AF), the representative R-R interval and/or the representative HR as determined by the IMD, and a duration of the arrhythmic episode. For instance, the IMD may be configured such that whenever it detects an arrhythmic episode, it saves (aka records) two values for the episode, such as a representative R-R interval (or a representative HR) for the episode, and a duration of the episode. Various different techniques which are known in the art (or developed in the future) may be used by the IMD to detect and classify various different types of cardiac arrhythmias, as well as to determine durations of the various different types of cardiac arrhythmias. In some embodiments, at the same time that the EGM segment data is transmitted to and obtained by an external system in communication with the IMD, either directly or indirectly (e.g., with a programmer or bedside monitor acting as an intermediary), the diagnostic log is also obtained by the external system from the IMD, and the external system (e.g., a server) links the EGM segment data for each episode to its corresponding representative R-R interval (and/or the representative HR) and a corresponding episode duration.

By way of example, where the arrhythmic episode is a bradycardia type of arrhythmic episode, the representative R-R interval (or the representative HR) can be a longest R-R interval (or equivalently, a slowest HR) during the bradycardia episode. Where the arrhythmic episode is a tachycardia type of arrhythmic episode, the representative R-R interval (or the representative HR) can be a shortest R-R interval (or equivalently a fastest HR) during the tachycardia episode. Where the arrhythmic episode is an AF type of arrhythmic episode, the representative R-R interval (or the representative HR) can be a mean (aka average) R-R interval or (equivalently a mean HR) during the AF episode. Where the arrhythmic episode is a cardiac pause type of arrhythmic episode, the representative R-R interval (or the representative HR) can be a longest R-R interval during the cardiac pause episode or the representative HR that is fastest. Other variations are also possible and within the scope of the embodiments described herein.

As further detailed below and as illustrated, for example, in FIGS. 3A and 3B, EGM segment data of the classified EGM datasets can include temporal information, morphological information and/or frequency information about the EGM segment, which information enables the EGM segment to be reproduced for display to medical personal, and enables the EGM segment data to be analyzed in accordance with the systems and methods described herein, e.g., for the purpose of ranking the arrhythmic episode corresponding to the EGM segment data, determining whether the arrhythmia detection was a true positive or a false positive detection, determining whether the arrhythmic episode should be reclassified is being a different type of arrhythmia than originally classified, and/or the like. As further detailed below, and as illustrated (for example) in FIGS. 3A and 3B, and FIGS. 4 and 5, such processing, analyses, and reclassifications may be accomplished by a server system utilizing one or more machine-learning (ML) models that may be applied to the classified EGM datasets that were generated by the IMD and then transmitted to the server system. Examples of the types of arrhythmias that may be specified by the respective IMD classification data were described above.

A classified EGM dataset for an arrhythmic episode can also include respective marker data for one or more of the markers described above, but not limited thereto. Where an ICM or other type of IMD detects an arrhythmic episode, it can be said that a detection of the arrhythmic episode was triggered by the IMD.

Referring back to FIG. 2, the ICM 100 is further equipped with a communication modem (modulator/demodulator) 140 and a telemetry circuit 164 (transmitter/receiver) to enable wireless communication. In one implementation, the communication modem 140 and the telemetry circuit 164 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician. Exemplary details of the telemetry circuit 164 are discussed below.

The ICM 100 also includes a sensing circuit 144 selectively coupled to one or more electrodes that perform sensing operations (optionally through the switch 127) to detect cardiac activity data indicative of cardiac activity. The sensing circuit 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, the switch 127 may be used to determine the sensing polarity of the cardiac signal by selectively closing the appropriate switches.

The output of the sensing circuit 144 is connected to the microcontroller 121 which, in turn, determines when to store EGM segment data for an EGM signal (digitized by the A/D data acquisition system 150) in the memory 160. For example, in certain embodiments, the microcontroller 121 only stores EGM segment data (from the A/D data acquisition system 150) in the memory 160 when a potential arrhythmic episode is detected. The sensing circuit 144 receives a control signal 146 from microcontroller 121 for purposes of controlling the gain, threshold, polarization charge removal circuitry (not shown), and the timing of any blocking circuitry (not shown) coupled to the inputs of the sensing circuit.

Optionally, the ICM 100 may include multiple sensing circuits, similar to sensing circuit 144, where each sensing circuit is coupled to two or more electrodes and controlled by the microcontroller 121 to sense cardiac electrical activity detected at the corresponding two or more electrodes. The sensing circuit 144 may operate in a unipolar sensing configuration or in a bipolar sensing configuration. Optionally, the sensing circuit 144 may be removed entirely and the microcontroller 121 perform the operations described herein based upon the EGM signals from the A/D data acquisition system 150 directly coupled to the electrodes.

The ICM 100 further includes an analog-to-digital A/D data acquisition system (DAS) 150 coupled to one or more electrodes via switch 127 to sample cardiac activity signals (e.g., EGM signals) across any pair of desired electrodes. The data acquisition system 150 is configured to acquire cardiac EGM signals (or segments thereof), convert the raw analog data into digital data, and store the digital data as EGM data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential arrhythmic episodes. Arrhythmia detection algorithms implemented and executing in the IMD may be applied to EGM signals received from the sensing circuit 144 and/or the DAS 150.

By way of example, the external device 154 may represent a bedside monitor installed in a patient's home and utilized to communicate with the ICM 100 while the patient is at home, in bed or asleep. The external device 154 may alternatively be a programmer (electronic device) used in a clinic to interrogate the ICM 100, retrieve data and program detection criteria and other features. The external device 154 may alternatively be a handheld device (e.g., smartphone, tablet device, laptop computer, smartwatch and the like) that can be coupled over a network (e.g., the Internet) to a remote monitoring service, medical network and the like. Other variations are also possible and within the scope of the embodiments described herein.

As described in further detail below, and with respect to FIGS. 3A and 3B, the external device 154 may be informationally connected (aka communicatively coupled) to a server system (e.g., a cloud-based server system) configured to receive a plurality of classified EGM datasets (EGM segment data and associated classifications) and to process those datasets utilizing a machine-learning (ML) model, thereby generating a plurality of machine-adjudicated EGM datasets that may further be used to generate diagnostic information and/or to provide for display a subset of machine-adjudicated EGM datasets determined (by the ML model) as having prioritized clinical relevance. In this manner, the external device 154 may be configured to facilitate access by clinicians to IMD patient data obtained over a period of time, as well as configured to permit a physician to review real-time EGM signals sensed by the ICM 100 or other type of IMD.

Referring back to FIG. 2, the microcontroller 121 is coupled to the memory 160 by a suitable data/address bus 162. The programmable operating parameters used by the microcontroller 121 are stored in the memory 160 and used to customize the operation of the ICM 100 to suit the needs of a particular patient. Such operating parameters define, for example, detection rate thresholds, sensitivity, automatic features, arrhythmia detection algorithms and criteria, activity sensing or other physiological sensors, and electrode polarity, but not limited thereto. As further described below (and with respect to e.g., FIGS. 3A and 3B and FIG. 6), the system and methods described herein permit a clinician to reprogram such operating parameters based upon the application of an ML model to the classified EGM datasets, and to view a selected, prioritized subset of machine-adjudicated EGM datasets (further described below) generated by applying the ML model to the classified EGM datasets, as well as view diagnostic information derived from the machine-adjudicated EGM datasets.

Referring again to FIG. 2, the memory 160 of the ICM 100 stores EGM datasets (i.e., cardiac activity data), as well as the markers and other data content associated with detection of arrhythmic episodes. The operating parameters of the ICM 100 may be non-invasively programmed into the memory 160 through the telemetry circuit 164 in telemetric communication via a communication link 166 with an external device 154. The telemetry circuit 164 allows EGM segment data, classification data, etc., and status information relating to the operation of the ICM 100 (as contained in the microcontroller 121 and/or the memory 160) to be sent to the external device 154 through the established communication link 166. In accordance with certain embodiments described herein, the telemetry circuit 164 conveys the classified EGM datasets and other information related to arrhythmic episodes to the external device 154.

The ICM 100 may further include magnet detection circuitry (not shown), coupled to the microcontroller 121, to detect when a magnet is placed over the ICM. A magnet may be used by a clinician to perform various test functions of the ICM 100 and/or to signal the microcontroller 121 that the external device 154 is in place to receive or transmit data to the microcontroller 121 through the telemetry circuit 164.

The ICM 100 can further include one or more physiologic sensors 170. Such sensors are commonly referred to (in the pacemaker arts) as "rate-responsive" or "exercise" sensors. The physiological sensor(s) 170 may further be used to detect changes in the physiological condition of the heart (or other muscle tissue for other, non-cardiac type IMDs), or diurnal changes in activity (e.g., detecting sleep and wake states). Signals generated by the physiological sensor(s) 170 are passed to the microcontroller 121 for analysis and optional storage in the memory 160 in connection with the cardiac activity data, markers, episode information and the like. While shown as being included within the housing 102, the physiologic sensor(s) 170 may be external to the housing 102, yet still be implanted within or carried by the patient. Examples of physiologic sensors might include sensors that sense, for example, activity, temperature, respiration rate, pH of blood, ventricular gradient, activity, position/posture, minute ventilation (MV), and so forth. Examples of such physiologic sensors include accelerometers, temperature sensors, microphones, and/or the like.

As shown in FIG. 2, a battery 172 provides operating power to all of the components in the ICM 100. The battery 172 is preferably capable of operating at low current drains for long periods of time. The battery 172 also desirably has a predictable discharge characteristic so that elective replacement time can be detected. As one example, the ICM 100 includes one or more lithium/silver vanadium oxide batteries. The battery 172 may afford various periods of longevity (e.g., three years or more of device monitoring). In alternate embodiments, the battery 172 could be rechargeable.

In some embodiments of the present disclosure, the ICM 100 provides a simple-to-configure data storage option to enable physicians to prioritize data based on individual patient conditions, to capture significant events and to reduce risk that unexpected events are missed. The ICM 100 may be programmable for pre- and post-trigger event storage. For example, the ICM 100 may be automatically activated to store 10-120 seconds of EGM segment data prior to an event of interest (e.g., an arrhythmia event) and/or to store 10-120 seconds of post EGM segment data. Optionally, the ICM 100 may afford patient triggered activation in which pre-event EGM segment data is stored, as well as post event EGM segment data (e.g., pre-event storage of 1-15 minutes and post-event storage of 1-15 minutes). Optionally, the ICM 100 may afford manual (patient triggered) or automatic activation for EGM segment data. Optionally, the ICM 100 may afford additional programming options (e.g., asystole duration, bradycardia rate, tachycardia rate, tachycardia cycle count). The amount of EGM segment data storage may vary based upon the size of memory 160, as well as other factors.

IMD Alerts

In some embodiments, the IMD software/firmware includes an urgent alert function that serves to mitigate problems associated with lost and/or overwritten classified EGM datasets when IMD memory (e.g., memory 160) reaches (or comes within a specified threshold of reaching) full capacity. For example, in one embodiment, one type of urgent alert comprises an "EGM memory is full" signal, which is processed by the IMD to treat the space occupied by previously read episodes (i.e., classified EGM datasets that have been transmitted to an external device for further processing) as available for rewriting. This urgent alert feature permits the IMD to capture new data without having to clear old data (as clearing adds complexity), as well as trigger an automated data transfer out of IMD memory when IMD memory is full or close to reaching capacity, for EGM data that had not yet been transmitted to an external storage and data processing system (or other external device/system).

In one embodiment, the urgent alert "EGM memory is full" signal is configured to ensure that the classified EGM datasets (and related data) stored in local memory (e.g., 160) of the IMD is transferred to an external storage and data processing system (or other external device/system), such as the server system described below, once a threshold for available free space is under a default setting of X % (e.g., 15%), or once a threshold amount (e.g. 85%) of the memory is already full. Such a method increases a likelihood that IMD data will be transmitted to the server system without a loss of data.

Alternatively, or additionally, in some embodiments, the IMD may be configured to push notifications to a patient (via, e.g., a patient mobile phone app) whenever implanted IMD advertising pings are not observed by the external device (e.g., 154) for a configurable duration, e.g., more than 8 hours. Such push notifications will help remind the patient to take active measures so that the IMD is capable of transmitting its stored classified EGM datasets and related information to the remote device/system and further ensure that the patient's EGM data, or a portion thereof, is not lost.

Diagnostic Information and Diagnostic Alerts

In some embodiments, the ICM 100 (or other type of IMD) may provide comprehensive diagnostic information including a summary of heart rate data, in order to assist physicians in diagnosis and treatment of patient conditions. By way of example, diagnostic information may include episode diagnostics for auto-trigger/alert events, episode duration, episode count, episode date/time stamp and heart rate histogram data.

In other embodiments, and as further described below, such episode diagnostic data and information is computed, processed, and stored by a server system configured to receive classified EGM datasets corresponding to arrhythmic episodes detected by an IMD (e.g., ICM 100), via external device 154 configured to be in communication with both the IMD and the server system (as further described below). In such other embodiments, and as further described below, IMD diagnostics management is improved by the systems and methods of the present disclosure, by using one or more machine-learning (ML) models implemented on a remotely located external storage and processing system. Using ML models and an external storage and processing system mitigates the potential for errors in diagnostic information which can arise from insufficient memory in the IMD, missing data records in the IMD, and/or inaccurate classifications of the EGM signals detected by the IMD (e.g., false positive IMD classifications or misclassified arrhythmic episodes). In addition, and as further described below, results of applying the ML models and related additional processing features of the present system (e.g., the handling of missing data records in the IMD, and/or inaccurate classifications of the EGM signals detected by the IMD) enable the system to provide diagnostic alerts to a clinician using the systems and methods described herein for improved patient monitoring and treatment protocols/interventions.

System Architecture and Functionality

FIGS. 3A and 3B illustrate high-level overviews of a system and methods configured in accordance with certain embodiments of the present technology. As shown in FIG. 3A, an IMD 300 is configured to transmit classified EGM data to an external storage and processing system 350, which may be an external device or a server system comprising one or more computers, a cloud-based server, and/or a virtual server. External storage and processing system 350 further includes (1) a data store 313 configured to store a database of patient database records, wherein the database may include a longitudinal database, and (2) a data processor (processing hardware, software, and/or firmware), which is configured to apply a machine-learning (ML) model to the classified EGM data (blocks 304 and 305, as further described below). The external storage and processing system 350 is sometimes referred to herein more succinctly as the system 350. The IMD 300 shown in and discussed with reference to FIG. 3A can be, e.g., the ICM 100 discussed above, but is not limited thereto.

As illustrated in the embodiment of FIG. 3A, and as further described below, processing the classified EGM datasets at external storage and processing system 350 generates machine-adjudicated EGM datasets 314 and/or diagnostic information 315, which are then provided for display to a clinician via a display device of or external to the system 350, for example, a laptop, tablet, or computer workstation (see block 307). Results of data processing by the system 350 are also optionally used to reprogram the IMD to improve its performance, for example, to reduce false positives (see block 308, further described below) and/or increase true positives. In accordance with certain embodiments, data processing results are also further used to update patient database records stored in database 313 (see block 305).

Thus, referring to FIG. 3A, at block 301, an EGM signal is analyzed over a period of time by one or more arrhythmia detection algorithms implemented by the IMD 300, and more specifically, one or more processors thereof. When an arrhythmia is identified in the EGM signal, one or more classified EGM datasets are generated by the arrhythmia detection algorithm(s) and recorded (i.e. stored) in the IMD's memory, including device documented (DD) markers designating signal features of interest within the EGM segment data, and associating EGM segment data with IMD classification data (aka IMD classification), such as, e.g., a classification of a type of arrhythmic episode and/or the nature of the arrhythmia. By way of example, one classified EGM dataset may be recorded in connection with a single arrhythmic episode, where the EGM segment data may correspond to an initial portion of the arrhythmic episode (e.g., the first 30 seconds or one minute). Additionally, or alternatively, EGM segment data of a distinct classified EGM dataset may correspond to another portion of the arrhythmic episode, such as the end portion of the arrhythmic episode or a segment of the arrhythmic episode exhibiting a particular characteristic of interest. The patient may experience numerous arrhythmic episodes over a day, week, month or otherwise. The IMD 300 continuously monitors the patient and records one or more classified EGM datasets in connection with each distinct arrhythmic episode, thereby forming a collection of classified EGM datasets associated with a corresponding collection of arrhythmic episodes over time. Each classified EGM dataset for an arrhythmic episode can include, e.g., respective EGM segment data and respective classification data for the arrhythmic episode, and may also include marker data, date/time stamps, and/or other identifying information associated with the arrhythmic episode. For a system in which the IMD 300 is an ICM, each classified EGM dataset for an arrhythmic episode can also include a representative R-R interval and/or a representative heart rate (HR) for the episode, as well as duration data indicative of the duration of the episode.

Additionally or alternatively, in the case where the IMD 300 is an ICM, the IMD 300 may also identify normal sinus rhythms and record one or more device classified normal sinus (DCNS) datasets, each of which can include EGM segment data collected in response to a determination by an ICM that a sensed EGM signal is indicative of a normal sinus rhythm, and one or more device documented markers related to one or more features of interest in the EGM segment that in whole or in part was utilized by the ICM to determine the DCNS classification. Such one or more DCNS datasets can be utilized as reference or baseline information for other analysis. The classified EGM datasets and the DCNS datasets can be referred to herein collectively or individually as device classified (DC) datasets.

As shown at block 303 in FIG. 3A, a plurality of classified EGM datasets 302 (302-1, . . . , 302-i, . . . ) (and/or DCNS datasets), which are stored within the IMD's memory (e.g., 160 of the ICM, or other type of IMD), are periodically transmitted to the external storage and processing system 350. In some embodiments, and at various points in time, the IMD 300 establishes a communication session with an external device (e.g. 154, FIG. 2), during which the opportunity arises to upload the recorded classified EGM datasets from the IMD to the external device (e.g., 154), for subsequent transmission to external storage and processing system 350, which may be remotely located. In the embodiment shown, at block 303, a plurality of classified EGM datasets are wirelessly transmitted from the IMD 300 to a local external device (e.g., 154) and/or a remote server. For example, and as further described below, the IMD 300 can be configured to wirelessly transmit classified EGM datasets to a bedside monitor installed in a patient's home, and the bedside monitor can in-turn retransmit (aka forward) the classified EGM datasets over a network (e.g., the Internet) to a remote monitoring service, medical network and/or the like operating the external storage and processing system 350. In such a case, the bedside monitor acts as an intermediate communication device between the IMD and a remote monitoring service, medical network and/or the like. Other types of external devices 154 can be used as an intermediate communication device, in place of the bedside monitor, such as smartphone, tablet device, laptop computer, smartwatch and/or the like, which can be coupled over a network (e.g., the Internet) to a remote monitoring service, medical network and/or the like.

In some embodiments, at least three types of transmissions of classified EGM datasets may occur at block 303, wherein each of the types of transmissions involve transmitting all of the classified EGM datasets that were stored by the IMD 300 since the last transmission. These three types of transmissions of classified EGM datasets include: (1) scheduled transmissions, (2) alert transmissions, and (3) patient-initiated transmissions. The scheduled transmissions are periodic transmissions that automatically initiate at the end of a programmable period, e.g., at the end of each day, week, or month, but not limited thereto. The alert transmissions are automatically initiated when the IMD detects that a configurable alert condition has been met, e.g., an AF episode lasting longer than 6 hours occurred in a single day, or EGM memory is full or close to being full, but not limited thereto. The patient-initiated transmissions are initiated in response to a patient using an external device, such as a bedside monitor or smartphone, to initiate the transmission. For example, a patient may initiate a transmission in response to experiencing symptoms of an arrhythmia.

Each transmission of the collection of classified EGM datasets stored in an IMD includes EGM segment data and IMD classification data for all new EGM segment data, as well as corresponding episode metadata/identifying information, such as, for example episode duration and arrhythmia-specific representative heart rate or R-R interval. Each EGM segment data may include, for example, approximately 30 seconds pre-detection and 2 minutes post-detection for AF, with 30 seconds pre-detection and 30 seconds post-detection for tachycardia, bradycardia, and pause. Other variations are also possible and within the scope of the embodiments described herein.

In accordance with certain embodiments, once the plurality of classified EGM datasets have been transmitted to an external device or server system (i.e., external storage and processing system 350), the portion of the IMD's memory (e.g., 160, FIG. 2) that had been used to store those classified EGM datasets can be overwritten with new classified EGM datasets.

At block 304, and as further described below with respect to FIG. 3B, an external device and/or remote server, which can collectively or individually be referred to as an external system, executes one or more machine-learning (ML) model processes to rank (aka prioritize) arrhythmic episodes and select, based on results of the ranking, arrhythmic episodes for which corresponding EGM segments are to be displayed to a clinician.

At block 305, and as further described below with respect to FIG. 3B, additional processing on the classified EGM datasets may include interpolating missing data from the EGM datasets to create machine-adjudicated EGM datasets, removing false positive classifications from the EGM datasets to create machine-adjudicated EGM datasets, updating database 313 with machine-adjudicated EGM datasets, and/or generating diagnostic information (DI) from the machine-adjudicated EGM datasets and storing such diagnostic information in database 313 (or some other data store of the external storage and processing system 350) for later evaluation and/or display to a clinician. Examples of such forms of additional processing are further described below.

At block 306, EGM segment data and/or related information (such as the aforementioned diagnostic information) are provided for display on a clinician's display device 307 for clinical evaluation. In some embodiments, block 306 may provide diagnostic information 315, including, e.g., a summary of heart rate and/or atrial fibrillation (AF) burden in order to assist physicians/clinicians in diagnosis and treatment of patient conditions. By way of example, diagnostic information 315 may include episode diagnostics for auto-trigger/alert events, episode duration, episode count, episode date/time stamp and heart rate histogram data.

Figure 6:
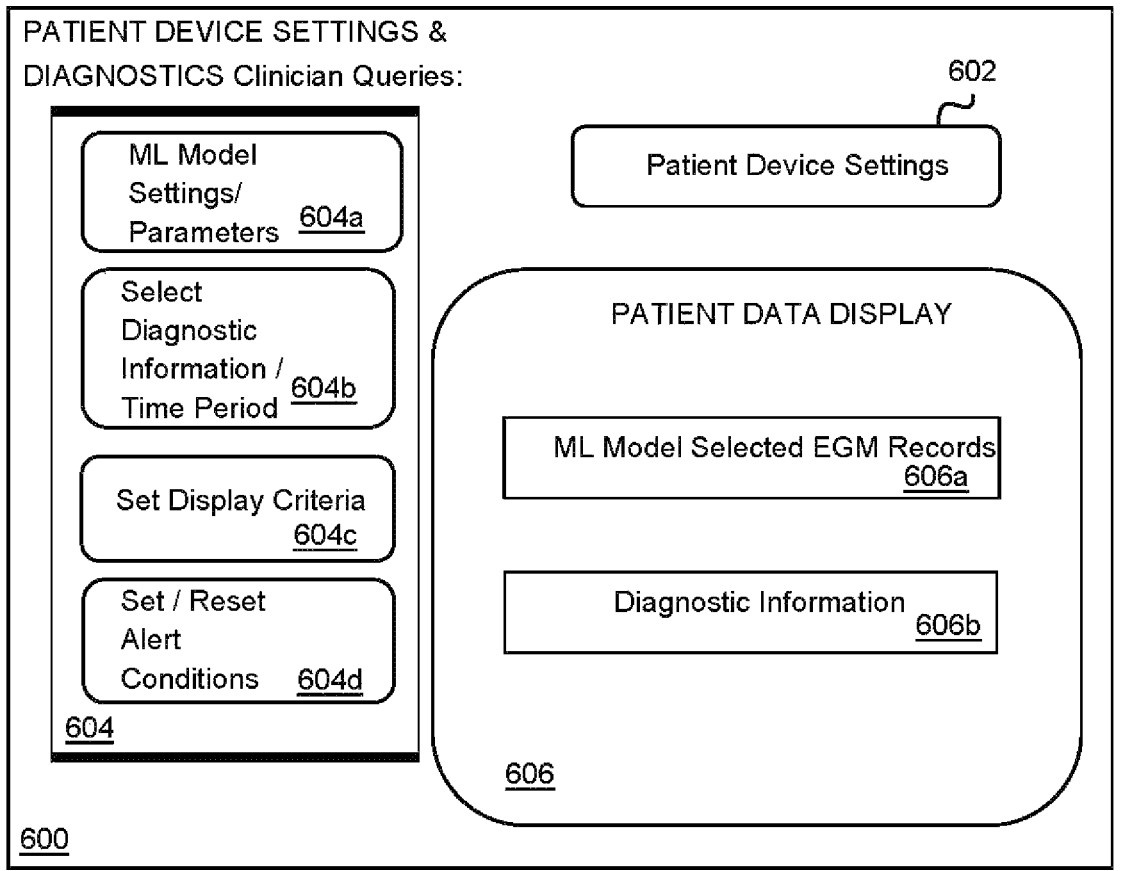
FIG. 6 shows a schematic diagram of one embodiment of a clinician's user interface to a system configured in accordance with certain embodiments described herein.

At block 308, which is optional, one or more sensing parameters and/or arrhythmia discrimination parameters of the IMD may be reprogrammed to reduce the probability of false positive detections of one or more types of arrhythmias. For cases in which the IMD is an ICM, such reprogramming may include, e.g., reducing a sensing threshold to reduce R-wave undersensing, and/or increasing a sensing threshold to reduce R-wave oversensing. Additionally, or alternatively, this can include adjusting morphology matching templates, arrhythmia discrimination algorithms, and/or the like. Further details of this optional aspect are described below with respect to an example clinician user interface as illustrated in FIG. 6. Example details of how an IMD can be reprogrammed are described in commonly assigned U.S. patent application Ser. No. 17/805,823, filed Jun. 7, 2022, titled "System And Method For Implantable Medical Device Remote Programming," which published as U.S. Patent Publication No. 2023/0054317, and which is incorporated herein by reference.

FIG. 3B illustrates further details of processing blocks 304, 305 and 306 of FIG. 3A. In the embodiment shown, blocks 304, 305 and 306 represent processes performed on an external device and/or remote server, which in some embodiments can collectively or individually be referred to as the external storage and processing system 350.

Referring to FIG. 3B, a plurality of classified EGM datasets 302 are received and stored in database 313. Block 304 executes instructions that apply one or more machine-learning (ML) model processes (block 304a) to determine a set of one or more confidence indicators (CI) associated with each classified EGM dataset, as described herein. The respective confidence indicator(s) are then used to assign a ranking score (RS) (aka prioritize) to each of the classified EGM datasets (block 304b) and, based on those ranking scores (RSs), identify (or select) one or more patient database records for which corresponding EGM segment data and/or related information are to be provided for display to a clinician (block 304c).

As further illustrated in FIG. 3B, results of applying the ML model processes 304a, 304b and 304c to the classified EGM datasets (e.g. confidence indicators (Cis) and ranking scores (RSs), and display identifications) are used to update patient database records comprising the classified EGM datasets 302, so as to include, for example, the respective CI and RS for each classified EGM dataset, and/or other identifying information determined by the ML model processes.

FIG. 3B further illustrates one embodiment of processing block 305 (shown generally in FIG. 3A), wherein the results of applying the ML model are further processed. In the embodiment of FIG. 3B, processing block 305 includes processes for updating patient database records by executing instructions to: (1) determine whether the classified EGM datasets 302 (which correspond to the plurality of arrhythmic episodes detected by the IMD during the period of time) includes a data signal temporal gap corresponding to missing information in the plurality of classified EGM datasets; (2) interpolate one or more approximate EGM dataset(s) suggested by the data signal temporal gap (block 305*a*); (3) store the approximate EGM dataset(s) in the database 313; (4) remove (or reclassify) false positive classifications from the classified EGM datasets; and/or (5) generate diagnostic information (DI) from at least one of the patient database records and the approximate EGM dataset(s) (block 305*b*). The plurality of machine-adjudicated EGM datasets may include one or more approximate EGM datasets, one or more reclassified EGM datasets, and/or a plurality of EGM datasets wherein one or more classified EGM datasets identified at block 304*a* as corresponding to a false positive classification has been removed at block 305*a*. Processes at block 305*a* may include data interpolation methods such as, for example, utilizing a "best polynomial fit" algorithm (with associated confidence bounds) when there is missing temporal data in the plurality of EGM datasets which would otherwise lead to a gap in diagnostic information, such as AF burden. In certain such embodiments, one such data interpolation method may include, for example, a polynomial fit algorithm applied to one or more previous periods of continuous data (i.e. a plurality of EGM datasets having no discernable temporal gaps) so as to determine a set of parameters (and associated confidence bounds) defining a polynomial corresponding to the one or more periods of continuous data, which polynomial can then be used to interpolate an approximate EGM dataset to be used for generating diagnostic information associated with the plurality of EGM datasets having missing temporal data. Interpolating an approximate EGM dataset (such as, for example, by assessing the polynomial fit) helps mitigate potential for errors in diagnostic information. (By way of example, see generally e.g., an application of polynomial fit to United States census data, including confidence bounds, as described at https://www.mathworks.com/help/matlab/data_analysis/programmatic-fitting.html.)

In the embodiment shown, database 313 is updated to include the plurality of machine-adjudicated EGM datasets determined at block 305*a* and the diagnostic information (DI) generated therefrom at block 305*b*.

Machine-Learning Models

The systems and methods described herein include and/or use an external storage and processing system (e.g., 350), such as a remote external device and/or a remote server, which in some embodiments is a cloud-based server system. The systems and methods of the present technology utilize one or more ML models to re-analyze a collection of classified EGM datasets corresponding to arrhythmic episodes detected and processed by an IMD (as, for example, described above). In some embodiments, a ML model identifies valid and invalid subsets of the classified EGM datasets (also referred to as appropriate and inappropriate subsets). The appropriate or valid subsets include device documented (DD) markers/IMD classifications that correctly characterize the corresponding EGM segment data, while the inappropriate or invalid subsets includes DD markers/IMD classifications that incorrectly characterize the corresponding EGM segment data. Stated another way, the appropriate or valid subset corresponds to true positive classifications of arrhythmic episodes, while the inappropriate or invalid subset corresponds to false positive classifications of arrhythmic episodes. In some embodiments, at block 306, information concerning the true positives classifications (or valid subset) is then provided for display to a clinician in various forms, as discussed herein.

Additionally, or alternatively, and as illustrated in FIG. 3B, the ML model may output a confidence indicator (CI) (e.g., a probability, likelihood, continuous value between 0 and 1) indicative of a level or degree of confidence that a distinct classified EGM dataset represents a true positive or false positive classification of an arrhythmic episode. As one example, the numeric indicator may be a continuous value between 0 and 1, where (a) the values close to zero indicate a high confidence that the EGM segment data of the classified EGM dataset is not indicative of an arrhythmia, and is thus a false positive, and (b) the values close to one indicate a high confidence that the EGM segment data of the classified EGM dataset is indicative of a correctly classified arrhythmic episode and is thus a true positive. When a classified EGM dataset is not indicative of an arrhythmic episode, the classified EGM dataset may include EGM segment data indicative of normal sinus rhythm or otherwise—for example, the EGM segment data within the classified EGM dataset may represent an unduly noisy signal that should not be otherwise characterized as an arrhythmia or a normal sinus rhythm.

In some embodiments, the ML model may include a detection threshold that may be changed/tuned by clinicians based on the clinician's needs and/or one or more various other factors. In the foregoing example, where numeric values near 1 indicate a high confidence of true positives and numeric values near 0 indicate a high confidence of false positives, the detection threshold may be lowered (e.g., closer to 0) to increase the sensitivity of the ML model. For example, when the detection threshold is set at 0.25, the ML model will identify more false positive classified EGM datasets, as compared to when the detection threshold is set at 0.75. For example, it may be desirable to apply a higher level of sensitivity in connection with certain types of critical arrhythmias that may not occur regularly. In addition, it may be desirable to apply a higher threshold, and thus lower the sensitivity, while increasing the specificity, in connection with other types of arrhythmias that are considered less "critical" to a patient's health and that may occur more often.

In accordance with certain embodiments, the arrhythmia detection algorithms operating on the IMD and the ML model(s) operating on the local external device and/or remote server afford two discriminators that work together to form a robust arrhythmia classification system. The system exemplified by embodiments shown in and/or described with reference to FIGS. 3A and 3B reduces false positive arrhythmias by implementing a machine-learning-based confirmation process to provide a second check with respect to IMD declared arrhythmias. The process described herein may be distributed between various devices (as, for example, devices shown in FIG. 8, described in further detail below), and more specifically, between one or more processors of one or more devices.

In some embodiments, the one or more processors may be further configured to analyze a distinct classified EGM dataset to extract one or more EGM signal features of interest from the EGM segment data (of the distinct classified EGM dataset), and to apply the one or more features of interest to the ML model. For example, when IMD 300 is an ICM, the one or more EGM signal features of interest may represent at least one of R-wave amplitude, R-wave amplitude variability, P-wave amplitude, P-wave amplitude variability, T-wave amplitude, T-wave amplitude variability, RR interval amplitude, RR interval amplitude variability, QRS area under the curve, or QRS area under the curve variability, and/or the like.

In some embodiments, the external storage and processing system 350 of the present disclosure implements and applies an ML model to generate identifying information for each classified EGM dataset. In some embodiments, such identifying information comprises one or more confidence indicators indicative of a degree of confidence, e.g.: (a) that the IMD classification included in the classified EGM dataset represents a true positive designation of the type of arrhythmic episode corresponding to the EGM segment; (b) that the IMD classification included in the classified EGM dataset represents a false positive designation of the type of arrhythmic episode corresponding to the EGM segment; (c) in an accuracy of identifying an EGM signal feature of the type of arrhythmic episode; (d) in a sensitivity level utilized by the IMD to identify one or more EGM signal features corresponding to the type of arrhythmic episode; and/or (e) of a degree of signal noise in the EGM segment data of the classified EGM dataset. The aforementioned identifying information can be stored, e.g., in the same database that stores the classified EGM datasets.

In some embodiments, identifying information also includes information obtained and recorded by the IMD, such as date/time stamps, and/or DD markers.

In some embodiments, identifying information also includes a machine-adjudicated reclassification of EGM segment data, in cases where application of the ML model has identified a false positive.

Figure 4:
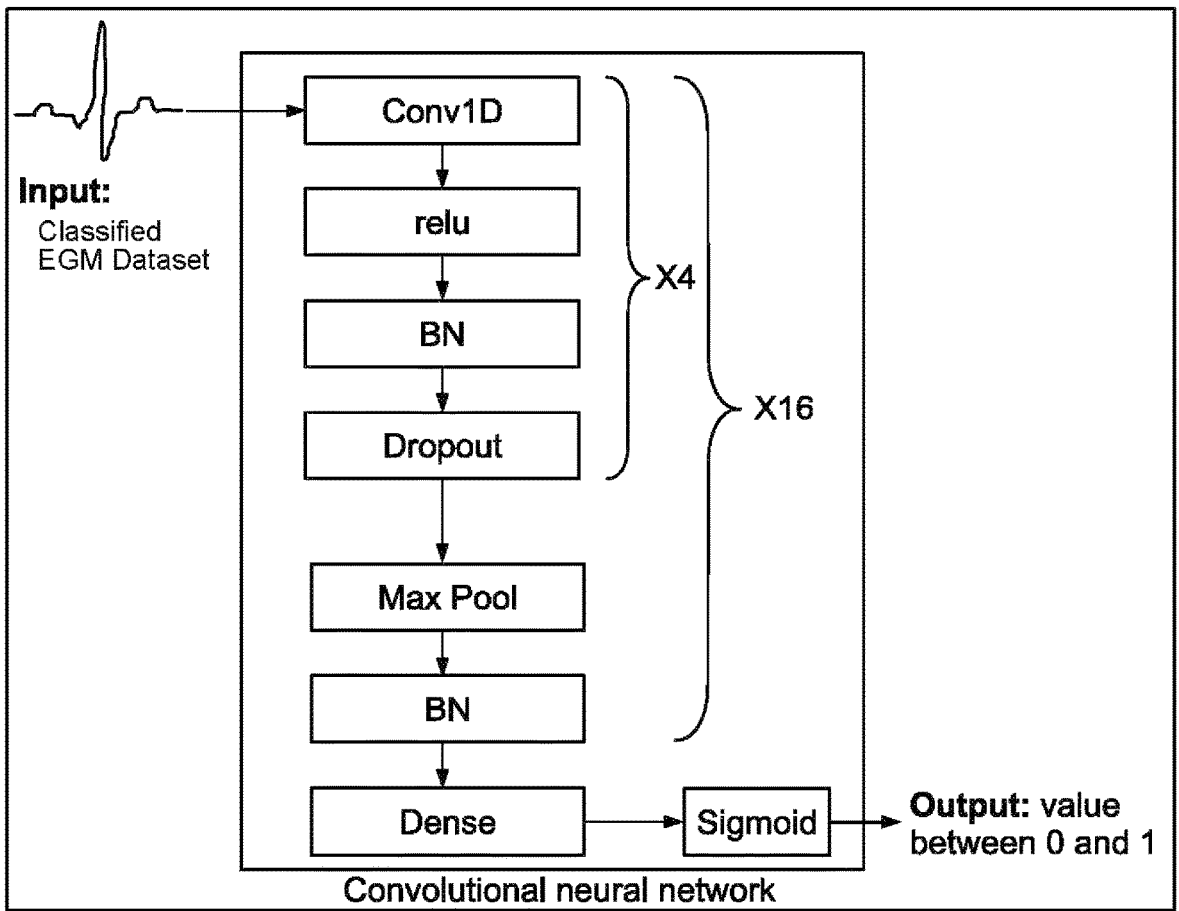
FIG. 4 illustrates a summary of an example machine-learning (ML) model that may be used in accordance with certain embodiments described herein.

FIG. 4 illustrates a summary of an example ML model that may be used in accordance with certain embodiments described herein. As shown in FIG. 4, the ML model includes a convolutional neural network architecture. It is recognized that the network architecture may differ and/or other types of machine-learning models may be utilized. In the present example, the ML model architecture of FIG. 4 is comprised of 16 network layers, each with 4 sub-layers followed by pooling and normalization. The architecture components include: 1-dimensional convolutional layers ("Conv1D"), rectified linear unit ("relu") activation functions, batch normalization ("BN"), etc. The network output is a continuous value between 0 and 1, where values close to zero indicate high confidence that EGM segment data does not correspond to an arrhythmic episode (e.g., is a false positive), and values close to 1 indicate high confidence of a true positive. As noted herein, the system may be tuned according to clinical needs. Further details, refinements, and alternatives to the ML model of FIG. 4, including methods for training such ML model, are described in U.S. patent application Ser. No. 17/341,436, titled METHODS AND SYSTEMS TO CONFIRM DEVICE CLASSIFIED ARRHYTHMIAS UTILIZING MACHINE LEARNING MODELS, which published as U.S. Patent Pub. No. 2022/0117538 A1, and which is incorporated herein by reference in its entirety.

In some embodiments, ML model operations may be repeated for different architectures of ML models. For example, when the ML model represents a convolutional neural network (CNN), various aspects of the CNN may be varied. For example, a first CNN may utilize a relu activation function, while a second CNN utilizes a leaky relu activation function, and a third CNN utilizes a sigmoidal activation function. Additionally or alternatively, a first CNN may utilize a first number of network layers, sublayers, hidden layers and the like, while a second CNN may utilize a second number of network layers, sublayers, hidden layers and the like, etc. In some embodiments, clinicians may choose to utilize their own classified EGM datasets and DCNS datasets to train ML models (as described in U.S. Patent Pub. No. 2022/0117538 A1, incorporated by reference above), such that the training data may be specific to a clinician, a single clinic, medical facility, medical network or otherwise. Additionally or alternatively, clinicians may choose to utilize a larger patient population of classified EGM datasets and DCNS datasets to train the ML models, such as by utilizing datasets collected by "trusted" third parties, or a combination thereof.

Optionally, the performance between ML models trained based on different augmented classified EGM datasets (as described in U.S. Patent Pub. No. 2022/0117538 A1) and/or different types/versions of models may be compared. For example, a clinician may apply the same augmented classified EGM datasets to a new version/type of ML model that were previously used with the prior ML model. The clinician may then be allowed to choose whether to use a newer version/types of ML model based on whether the performance is better than the prior model.

The trained ML model may provide various types of outputs, as mentioned above. In one example, the ML model may be trained to output an indication of whether a corresponding classified EGM dataset is valid (a true positive) or invalid (a false positive). (False positives, for example, this could be initially identified by running a recorded EGM signal through a device simulator with different device parameter settings, and finding the best settings that retains as many true detections as possible and removes the false ones.) Additionally, or alternatively, the ML model may be trained to output a confidence indicator (e.g., a probability, likelihood, continuous value between 0 and 1) indicative of a level or degree of confidence that an individual underlying classified EGM dataset represents a true positive or false positive designation of an arrhythmia. As one example, the numeric indicator may be a continuous value between 0 and 1, where the values close to zero indicate a high confidence that the EGM segment data corresponding to the classified EGM dataset is not indicative of an arrhythmia, and thus a false positive. The values close to 1 indicate a high confidence that the EGM segment data corresponding to the classified EGM dataset is indicative of an arrhythmia and thus a true positive. When a classified EGM dataset is not indicative of an arrhythmia, the classified EGM dataset may correspond to the EGM segment data indicative of normal sinus rhythm; or, the EGM segment data corresponding to the classified EGM dataset may exhibit an unduly noisy signal that should not be characterized as either an arrhythmia or a normal sinus rhythm. Thus, additionally or alternatively, the ML model may be trained to provide an output indicating that a particular classified EGM dataset is unduly noisy and should not be characterized as a normal sinus rhythm, nor an arrhythmia.

For the systems and methods of the present disclosure, the ML model can be trained to provide outputs in connection with each classified EGM dataset, including at least one confidence indicator indicative of a degree of confidence in the IMD classification of the classified EGM dataset, as described above. Additionally or alternatively, the ML model may be trained to include a detection threshold that may be changed/tuned by a clinician based on the clinician's needs and/or one or more various other factors. In the foregoing example, where numeric values near 1 indicate a high confidence of true positives and numeric values near 0 indicate a high confidence of false positives, the detection threshold may be lowered (e.g., closer to 0) to increase the sensitivity of the ML model. For example, when the detection threshold is set at 0.25, the ML model will identify more false positive classified EGM datasets, as compared to when the detection threshold is set at 0.75. A clinician may find, for example, that it may be desirable to apply a higher level of sensitivity in connection with certain types of critical arrhythmias that may not occur regularly. In addition, it may be desirable to apply a higher threshold, and thus lower the sensitivity, while increasing the specificity, in connection with other types of arrhythmias that are considered less "critical" to a patient's health and that may occur more often.

Diagnostic & Data Management Methods

FIG. 5 summarizes a process 500 for reducing clinical review burden of EGM datasets by managing their presentation in accordance with certain embodiments described herein, such as in the embodiment illustrated in and described with reference to FIGS. 3A and 3B. The operations of process 500 may be implemented, in whole or in part, by one or more processors of a local external device, remote server, and/or a combination thereof. By way of illustration, process 500 is described as being performed by external storage and processing system 350 (see FIG. 3A), in accordance with certain embodiments of the present technology.

Referring to FIG. 5, at Step 502, the system receives classified EGM datasets corresponding to arrhythmic episodes detected by an IMD during a period of time; each classified EGM dataset comprises (1) EGM segment data corresponding to an arrhythmic episode, and (2) an IMD classification for the arrhythmic episode. At Step 504, the system stores the classified EGM datasets in patient database records of a database. At Step 506, the system applies a machine-learning (ML) model to each classified EGM dataset of the patient database records, thereby determining a respective confidence indicator (CI) associated with each classified EGM dataset which indicates a degree of confidence relating to the IMD classification associated with the EGM segment data of the classified EGM dataset. At Step 508, the system then updates the patient database records so as to include, for each patient database record, the respective confidence indicator determined by the ML model. At Step 510, the system further assigns a ranking score to the patient database record, based upon the respective confidence indicator in comparison to a set of respective confidence indicators relating to a same type of arrhythmic episode and included in other patient database records. At step 512, based upon the ranking score assigned to each of the patient database records, the system identifies at least one patient database record for display. At Step 514, the system provides for display—on a display device in communication with the data processing system—the patient database record(s) identified for display.

FIG. 6 shows a schematic diagram of an example user interface 600 to or of a system configured in accordance with certain embodiments described herein. The blocks of FIG. 6 illustrate exemplary features that may be implemented in a user interface for a clinician's display device 307 (FIG. 3A), such as a tablet or laptop computer, which is informationally coupled to data processing system 350 (FIG. 3A). Input and output features of this example user interface 600 may be illustrated and understood with reference to the following illustrative steps facilitating possible clinician user interactions with the system architecture described above with respect to FIGS. 3A, 3B and 5:

1. A back-end server system receives, from a remote device, a plurality of classified EGM datasets, each classified EGM dataset comprising EGM segment data and an associated classification, and wherein the EGM segment data represents an arrhythmic episode detected and classified for a given patient by an implanted IMD during a period of time. Block 602 facilitates a clinician user to set and reset patient IMD device settings (e.g., device sensitivity settings, patient alert profile settings), as further described below (see FIG. 8). For example, for cases in which the IMD is an ICM, block 602 facilitates reprogramming the ICM, which may include, e.g., reducing a sensing threshold to reduce R-wave undersensing, and/or increasing a sensing threshold to reduce R-wave oversensing. Additionally, or alternatively, this can include adjusting morphology matching templates, setting arrhythmia discrimination algorithms, and/or the like. For example, in certain embodiments, sensing parameters for an ICM that may be reconfigured by a clinician user (to increase the probability that the ICM is correctly sensing an arrhythmic episode from the EGM signals sensed by the ICM) may include, for example, R-wave threshold (mV), refractory period (ms), refractory decade delay (ms), and/or threshold start (%)). As further described below, in certain embodiments, such sensing parameters comprise a set of inputs to one or more arrhythmia discrimination algorithms used at the back end to adjust the effectiveness of the system described herein. Additionally, in some embodiments, the arrhythmia discrimination algorithms themselves may include configurable selections that permit the clinician user to influence a response on the receiver operating characteristic (ROC) curves for one or more arrhythmia discrimination algorithms, thereby rendering the algorithm(s) more sensitive and/or more specific, based on more sensitive, balanced or more specific setting choices.

2. The back-end server system stores the plurality of classified EGM datasets in a patient-specific portion of a longitudinal database.

3. A front-end application presents at user interface 600 a query (generated, e.g., by the back-end server system) to a clinician user (block 604), so as to obtain a set of patient-specific parameter settings configured to: (a) enable the machine-learning model to process a set of patient-specific longitudinal data relating to the set of arrhythmic episodes (block 604a); and (b) select a set of diagnostic information (block 604b) and a set of display criteria associated with a subset of machine-adjudicated EGM datasets to be displayed (block 604c).

4. The front-end application presents a second query (generated, e.g., by the back-end server system) to the clinician user, so as to obtain a set of alert conditions relating to one or more arrhythmic episodes for the patient-specific longitudinal data (block 604d). Such alert conditions may include, for example, setting a threshold level for a total number of false positives (as determined by the ML model applied to the classified EGM datasets) recorded by the IMD over a period of time, above which the system will provide for display a diagnostic alert (e.g., "too many false positives recorded by IMD"), and/or setting a similar threshold level for a total number of true positives (as determined by the ML model applied to the classified EGM datasets) detected by the IMD over a period of time, below which the system will provide for display another diagnostic alert (e.g., "too few arrhythmic episodes detected by IMD"), which would be beneficial, for example, in an AF population where the IMD is an ICM. This feature also allows the ability of the clinician user to create new diagnostic alerts that are not available through the device directly, such as, for example, a diagnostic alert relating to the presence of one or more data gaps (as identified and interpolated by the system's processing algorithms, described above), and/or a diagnostic alert relating to the rate of change over time for arrhythmic episodes detected by the IMD. By way of example, in certain embodiments, alert conditions may also include device alerts (e.g., battery low, parameter errors, monitor at end of service, device reset, monitoring disabled, etc.), and/or additional clinician alerts (such as, e.g. AF episode, continuous AF, AF burden, and/or arrhythmic episode type (tachycardia, bradycardia, etc.) when the IMD is an ICM.

5. The back-end server system then generates at least one assessment of an alert condition of the set of alert conditions, based upon the set of diagnostic information selected for display.

6. The back-end server system then conditionally resets the set of alert conditions based upon the at least one assessment.

7. A patient data display window 606 is presented on the user interface 600, which displays data and information generated by the system of the present disclosure, including (as illustrated in the example embodiments): (a) one or more machine-adjudications EGM datasets selected for display by the ML model(s) applied to the classified EGM datasets (block 606a) (see also e.g., 314 in FIG. 3A, and 304 in FIG. 3B); and (b) diagnostic information and alerts (block 606b) as described above with respect IMD alerts and diagnostic alerts, and further detailed below (see FIG. 8).

As described above, the systems and methods of the present disclosure may accept clinician user responses to one or more sets of user interface queries, which permit configurable, functional extensions to firmware that may be operating on an IMD. As described herein, the systems and methods of the present disclosure thereby enables a clinician user to reprogram and/or configure an IMD based upon analysis of diagnostic information generated by the system; the nature of such reprogramming/reconfigurations can be extended to include logic and values beyond the limitations of the deployed operating firmware in the IMD. This aspect allows a clinician, for example, to extend the concept of an alert from an on-off switch with firmware-limiting configurations to more nuanced means of detecting changes in a patient's status. For example, in a case where an IMD is an ICM, certain embodiments may allow a clinician to distinguish and record whether an AF burden over the past week has increased by 10%, versus an AF burden that increased only for a single day and recovered the next day (inconsequential to report as the patient is already optimally medically managed, and there is no clinical action to be taken). These nuanced differences thus permit more complex logic residing on the back end (server side) of the present system.

FIGS. 7A and 7B collectively illustrate a process 700 for analyzing data obtained from an IMD, and for managing the clinical presentation of such data in accordance with certain embodiments described herein, including, e.g., improving diagnostic alerts and/or summary diagnostic information generated for an IMD-implanted patient. The operations of process 700 may be implemented, in whole or in part, by one or more processors of a local external device, remote server, and/or a combination thereof. By way of illustration, process

700 is described as being performed by the external storage and processing system 350 (see FIGS. 3A and 3B).

Referring to FIGS. 7A and 7B, at Step 702, the system receives classified EGM datasets from a remote device, wherein each classified EGM dataset includes (1) EGM segment data and (2) an associated classification for an arrhythmic episode detected by an IMD during a period of time. At Step 704, the system stores the classified EGM datasets in a longitudinal database, or alternatively, some other type of database. At Step 706, using a machine-learning model, the system: (a) determines a set of true positive arrhythmic episodes detected by the IMD and generates a set of identifying information (e.g., as described above) for the true positive arrhythmic episodes, and (b) determines a set of false positive arrhythmic episodes detected by the IMD and generates a set of identifying information for the false positive arrhythmic episodes (which may indicate, if appropriate, the absence of any false positive detections). At Step 708, the system ranks the set of true positive arrhythmic episodes based upon the related set of identifying information to obtain a ranking score for each true positive. At Step 710, the system updates the longitudinal database to include the set of identifying information relating to the set of true positive arrhythmic episodes and the ranking score for each true positive arrhythmic episodes. At Step 712, the system removes from the longitudinal database each classified EGM dataset corresponding to a member in the set of false positive arrhythmic episodes, based upon the identifying information for the set of false positive arrhythmic episodes, thereby to obtain a plurality of machine-adjudicated EGM datasets from the plurality of classified EGM datasets. At Step 714, the system generates a set of diagnostic information (such as, for example, heart rate histogram data, episode diagnostics for auto-trigger/alert events, episode duration, episode count, and/or episode date/time stamp) based upon the plurality of machine-adjudicated EGM datasets. At Step 716, the system selects for display a subset of the machine-adjudicated EGM datasets, based upon the ranking scores and identifying information for the set of true positive arrhythmic episodes. At Step 718, the system provides for display: (a) the set of diagnostic information, and (b) the subset of machine-adjudicated EGM datasets comprising EGM segment data to be displayed.

In the foregoing examples, a distinct classified EGM dataset in the plurality of classified EGM datasets is described in connection with a series of beats-thus, a distinct classified EGM dataset includes distinct EGM segment data representing EGM signals for two or more beats, with corresponding EGM signal features of interest. In some embodiments, a distinct classified EGM dataset may correspond to a single beat, with one or more signal features of interest corresponding to EGM signal features within a single beat (e.g., R-wave, P-wave and/or T-wave peak, duration, area under the curve). In some embodiments, the ML model of the system and method presently disclosed may be configured in accordance with one or more of the methods disclosed in U.S. Patent Pub. No. 2022/0117538 A1 (incorporated herein by reference in its entirety; see, in particular, FIG. 6 and related description therein); such ML model is configured to perform beat level adjudication, wherein the ML model analyzes each distinct classified EGM dataset and, for example, determines whether the peak(s) of the R-wave, P-wave and/or T-wave were correctly identified and labeled with DD markers, thereby representing a true positive IMD classification for the EGM segment data.

Exemplary Cloud-Based, Distributed Data Processing System

Figure 8:
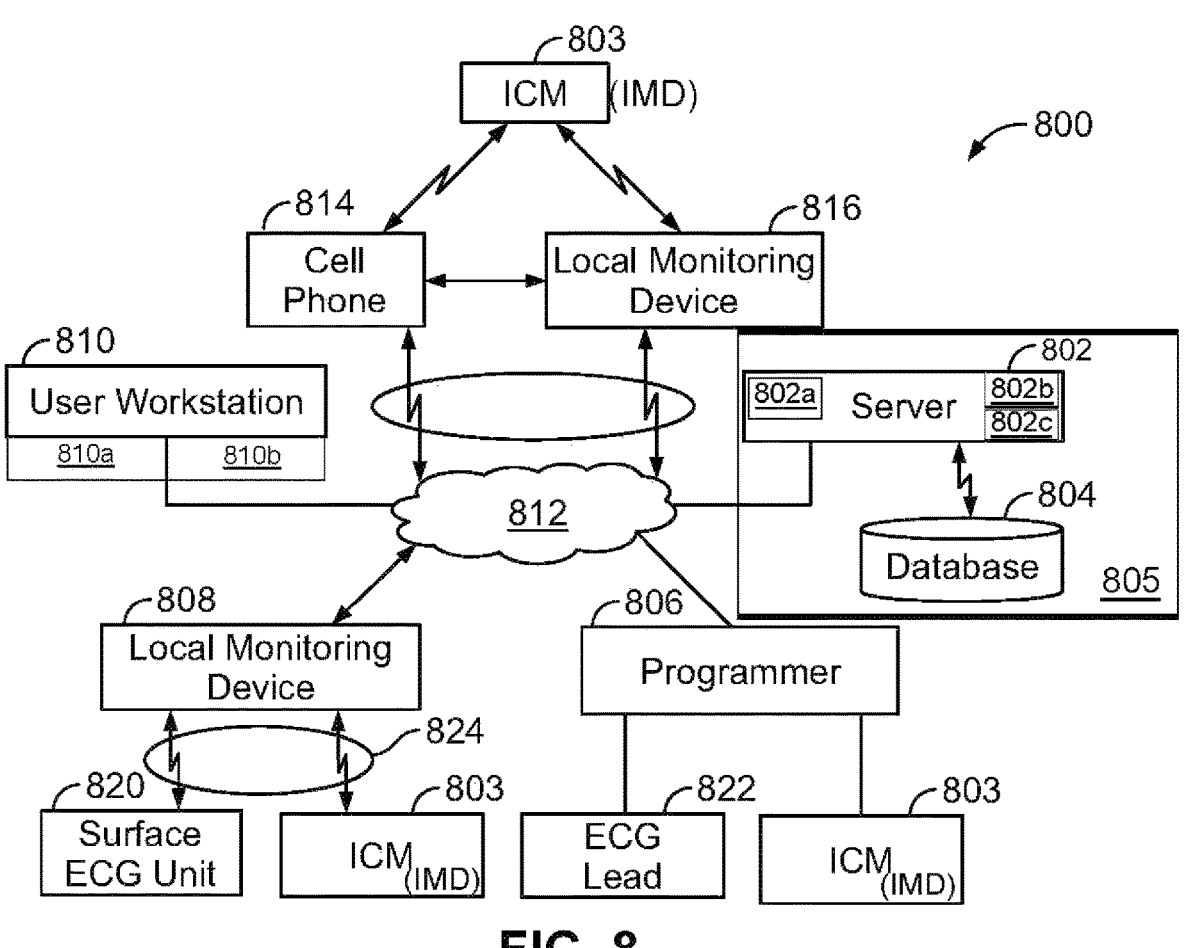
FIG. 8 illustrates a distributed processing system configured in accordance with certain embodiments described herein.

FIG. 8 illustrates a distributed data processing system 800 in accordance with certain embodiments described herein. Distributed data processing system 800 includes: a server 802 connected to a database 804; a programmer 806; a local monitoring device 808; and a user workstation 810 electrically connected to a communication network 812. Any of the processor-based components in FIG. 8 (e.g., workstation 810, cell phone 814, local monitoring device 816, server 802, and programmer 806) may perform one or more processes or steps discussed herein.

In some embodiments, data processing system of the present disclosure may include: (a) an IMD (e.g. ICM 100; IMD 300; ICM 803) configured to detect, record, process and transmit a plurality of signals corresponding to a plurality of classified EGM datasets representing a set of arrhythmic episodes, as classified by the IMD; (b) an external device (e.g. external device 154; cell phone 814; local monitoring device 816) configured to receive the plurality of signals from the IMD and to re-transmit the plurality of signals over a communication link (e.g., communication network 812) connected to the external device; and (c) a server system 805 informationally connected (aka communicatively coupled) to the external device via a communication link over communication network 812, where the server system 805 includes a server 802 having a network interface 802a and memory 802b configured to store (1) a first set of instructions corresponding to a machine-learning model configured to determine at least one confidence indicator relating to each classified EGM dataset in the plurality of classified EGM datasets, and to generate, for each classified EGM dataset, a machine-adjudicated EGM dataset including the at least one confidence indicator, (2) a second set of instructions configured to generate a set of diagnostic information based upon a plurality of said machine-adjudicated EGM datasets generated by the machine-learning model, and (3) a third set of instructions configured to select for display at least one machine-adjudicated EGM dataset from the plurality of said machine-adjudicated EGM datasets. In such an embodiment, the server system also includes one or more server processors 802c configured to execute the first, second and third sets of instructions to determine the at least one confidence indicator for each classified EGM dataset and to generate machine-adjudicated EGM datasets therefrom, as well as the set of diagnostic information based upon the machine-adjudicated EGM datasets, and to select for display a subset of machine-adjudicated EGM datasets from the plurality of said machine-adjudicated EGM datasets.

In such embodiments, a database 804 of server system 805 (and/or external to it; see e.g., database 313 of FIG. 3A) is configured to store the plurality of machine-adjudicated EGM datasets in relation to the set of arrhythmic episodes and the set of diagnostic information. The server 802 of server system 805 further includes a network interface 802a configured to transmit signals representing the subset of machine-adjudicated EGM datasets to a display device, shown in FIG. 8 as a user workstation 810, comprising user input device 810a (e.g., a touch screen) and a front-end application programming interface (API) 810b, informationally connected (aka communicatively coupled) to the network interface 802a via communication network 812.

In the embodiment shown, server system 805 is a cloud-based system. A communication link over communication network 812 may comprise a hard-wired, and/or wireless communication link.

In some embodiments, IMD 803 of data processing system 800 is further configured to transmit an alert signifying a request to initiate transmission of the plurality of signals to the external device (as described above).

As described above, in some embodiments, data processing system 800 further includes data storage configured to save the plurality of classified EGM datasets, each classified EGM dataset representing an arrhythmic episode in the set of arrhythmic episodes, and the second set of instructions is executed to identify a temporal gap in the plurality of classified EGM datasets, interpolate an approximate EGM dataset suggested by the plurality of classified EGM datasets, and update the data storage to include the approximate EGM dataset along with the plurality of classified EGM datasets so as to mitigate potential for error in generating diagnostic information that may be associated with the temporal gap. In some embodiments, the data storage is a component of the database (313 or 804). In some embodiments, the database is a longitudinal database.

The communication network 812 may provide cloud-based services over the Internet, a voice over IP (VoIP) gateway, a local plain old telephone service (POTS), a public switched telephone network (PSTN), a cellular phone-based network, and the like. Alternatively, the communication network may be a local area network (LAN), a medical campus area network (CAN), a metropolitan area network (MAN), or a wide area network (WAM). The communication system serves to provide a network that facilitates the transfer/receipt of data and other information between local and remote devices (relative to a patient). In some embodiments, server 802 is a computer system that provides services to the other computing devices on the communication network 812.

In the embodiment shown, server 802 may be configured to control the communication of myriad information such as classified EGM datasets, EGM signals, motion data, bradycardia episode information, asystole episode information, arrythmia episode information, markers, heart rates, and device settings. In such embodiments, server 802 interfaces with the communication network 812 to transfer information between the programmer 806, local monitoring devices 808, 816, user workstation 810, cell phone 814 and database 804. For example, server 802 may receive classified EGM datasets from various clinics, medical networks, individual patient's and the like, and utilize the classified EGM datasets to train new ML models, update existing versions of ML models and add further outputs to existing and new ML models. The server 802 may further push new ML models and/or updated versions of ML models to various other devices, such as the programmers, local monitoring devices, cell phones, workstations and the like, illustrated in FIG. 8. The database 804 is configured to store machine-adjudicated EGM datasets and myriad associated information, such as classified EGM datasets, arrhythmia episode information, arrythmia statistics, diagnostic information, DD markers, raw EGM segment data, heart rates, device settings, and the like, for a patient population, as well as separated for individual patients, individual physicians, individual clinics, individual medical networks and the like.

In accordance with embodiments described herein, server 802 is configured to implement ML training operations in connection with training one or more ML models incorporated into the system and methods of the present disclosure (e.g. as illustrated in FIGS. 3A-3B and FIGS. 4-5), and/or utilize the ML models to analyze the subsequent classified EGM datasets as described in connection with FIGS. 5 and 7. Database 804 (313) may also be configured, in some embodiments, to maintain the ML models as they are trained and updated for use in the system and methods described herein. In such embodiments, the ML models and other information are downloaded, for example, into the database 804 via the server 802; or, alternatively, the information is uploaded to the server 802 from the database 804.

Programmer 806 may reside in a patient's home, a hospital, or a physician's office. The programmer 806 may wirelessly communicate with the IMD 803 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 806 to the IMD 803. In such case, programmer 806 is able to acquire information from surface electrodes on a person (e.g., ECG lead 822), EGM signals from the IMD 803, and/or classified EGM datasets, arrythmia episode information, arrythmia statistics, diagnostic information, markers, EGM signal waveforms, atrial heart rates, and device settings from the IMD 803. The programmer 806 interfaces with communication network 812 (e.g., via the Internet) to upload/transmit signals and information acquired from the surface ECG unit 820 (or ECG lead 822), or the IMD 803, to the server 802.

The local monitoring device 808 interfaces with the communication network 812 to upload/transmit to the server 802 one or more of the classified EGM datasets, EGM signals, motion data, arrythmia episode information, arrythmia statistics, diagnostics, markers, heart rates, sensitivity profile parameter settings and detection thresholds. In one embodiment, the surface ECG unit 820 and the IMD 803 have a bi-directional connection 824 with the local RF monitoring device 808 via a wireless connection. The local monitoring device 808 is able to acquire surface ECG signals from an ECG lead 822, as well as classified EGM datasets and other information from the IMD 803. On the other hand, the local monitoring device 808 may download data and information discussed herein (such as IMD settings) from the database 804 to the IMD 803, in connection with programming/reprogramming the IMD (as described above).

The user workstation 810, cell phone 814 and/or programmer 806 may be utilized by a physician, clinician, or other medical personnel to interface with communication network 812 to download/transmit patient database records, machine-adjudicated EGM datasets and/or related diagnostic information, as described herein, from the database 804 (among other functions, e.g., to obtain data and information directly or indirectly from the local monitoring devices 808, 816, from the IMD 803 or otherwise). Once such data and information are downloaded, user workstation 810 may process and/or display EGM datasets, signals and information in accordance with one or more of the embodiments as described above.

For example, user workstation 810, cell phone 814 and/or programmer 806, may be used to present information from patient database records such as ML-ranked EGM datasets, including confidence indicators, and machine-adjudicated EGM datasets, and/or diagnostic information concerning at least one arrhythmic episode of at least one patient to a physician/clinician.

Additionally or alternatively, user workstation 810, cell phone 814 and/or programmer 806 may be utilized to display a user interface presenting input queries that enable a physician/clinical to: (a) set/reset patient device settings; (b) set/reset ML model settings and parameters; (c) select diagnostic information for analysis and/or display (including a time period for the analysis); (d) set/reset display criteria or key episodes); and (e) set/reset alert conditions for a patient. In some embodiments, user workstation 810, cell phone 814 and/or programmer 806 may upload/push device settings (e.g., sensitivity profile parameter settings), IMD instructions, other information and notifications to the cell phone 814, local monitoring devices 808 (816), programmer 806, server 802 and/or IMD 803. For example, user workstation 810 may provide instructions to the IMD 803 in order to update sensitivity profile parameter settings when IMD 803 determines that the motion data is indicative of at least one of a posture change or a respiration cycle that reduced the amplitude of the EGM signals under certain circumstances.

Figure 9:
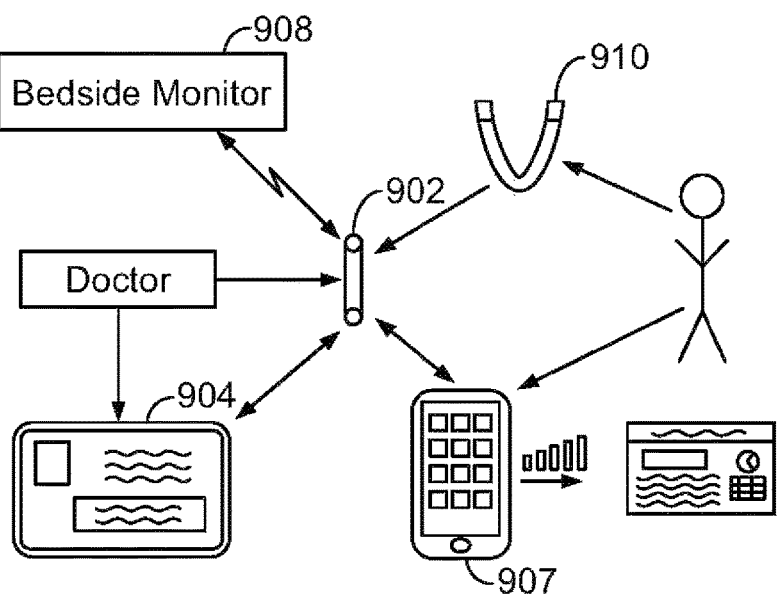
FIG. 9 illustrates a system level diagram indicating potential devices and networks that utilize the methods and systems described herein.

Various features and functionalities of one comprehensive embodiment of data processing system 800 for one exemplary embodiment is now described. Referring to FIG. 8, in one embodiment, server system 805 of data processing system 800 is a cloud-based server system configured to receive a transmission of EGM signals from a remotely located, local monitoring device 808 (or 816), where the transmitted EGM signals represent EGM patient data recorded and classified by IMD 803 implanted in a patient (as shown in FIG. 9, further described below). In this embodiment, collection, recordation, classification and transmission of EGM signals is accomplished using existing IMD methods, such as those described above (see also e.g., description of FIG. 2). In this embodiment, server system 805 generally performs the following features of the present technology:

i. Server system 805 receives a transmission of signals representing classified EGM datasets recorded and classified by IMD 803.

ii. Server system 805 causes a query to be presented to a clinician via user workstation 810, to obtain a set of patient-specific custom settings that are configured by the clinician via, for example, a user input device 810$a$ and a front-end API 810$b$. The patient-specific custom settings influence how to assess the IMD memory contents. Such configurations could include, for example, enabling ML adjudication, enabling key episodes, setting thresholds for new alert capabilities that do not exist in the IMD (e.g., assessing AF burden greater than 25% over a set time period, etc.).

iii. The patient-specific custom settings (query results) and the classified EGM datasets are then input to algorithms embodied as computer programming instructions executing on one or more processors of server 802, where those instructions are configured to:

(a) decode the EGM signals so as to form a set of patient database records comprising classified EGM datasets that are then stored in database 804 of server system 805;

(b) adjudicate each classified EGM dataset (which corresponds to an IMD-detected arrhythmic episode) using one or more trained ML models (as described above), assessing each arrhythmic episode (e.g., bradycardia, pause, AF, tachycardia episode for the case where IMD 803 is an ICM) as a true positive or as a false positive based on validated performance of the trained ML model(s)—this ML-adjudication step results in a set of machine-adjudicated EGM datasets comprising one or more confidence indicators for each classified EGM dataset;

(c) store the machine-adjudicated EGM dataset for each arrhythmic episode into database 804;

(d) remove, invalidate, or reclassify any false detection episodes, as identified from the ML-adjudication step, from the set of patient database records; and (e) rank the set of machine-adjudicated EGM datasets based upon their respective confidence indicator(s), for additional processing (e.g., generating diagnostic information relating to the patient) and for selecting for display to a clinician (on workstation 810) key episodes, using the ML rankings instead of, for example, episode duration and/or most recent episode as display criteria.

iii. Server system 805 causes a prompt to be presented to a clinician via workstation 810, configured to obtain a clinician-configurable time period (examples include since last clearing/since last read/last 30 days); the results are then input to algorithms embodied as computer programming instructions executing on one or more processors of server 802, where those instructions are configured to:

(a) access database 804 to obtain previously machine-adjudicated EGM datasets across multiple transmissions for the time period configured by the clinician;

(b) generate a set of diagnostic information using the accessed results, and cause to be displayed on workstation 810 such diagnostic information (e.g., as histogram data and/or trend data); and (c) reassess IMD alert conditions using the set of diagnostic information and update the IMD memory store to clear or reset the IMD alert conditions.

An aspect of the invention relates to a data processing system 350, 800 comprising one or more processors 802c and a memory 802b comprising instructions, which when executed by the one or more processors 802c, cause the one or more processors 802c to perform the method of the invention. In particular, the instructions stored in the memory 802b cause, when executed by the one or more processors 802c, the one or more processors 802c to store, in a respective plurality of patient database records of a database 313, 804, a plurality of classified electrogram (EGM) datasets corresponding to a plurality of arrhythmic episodes detected by an IMD 100, 300, 803, 902 during a period of time, wherein each classified EGM dataset comprises EGM segment data corresponding to one of the arrhythmic episodes and an IMD classification for the arrhythmic episode. The instructions also cause the one or more processors 802c to apply, in the data processing system 350, 800, a machine-learning model to each classified EGM dataset of the plurality of patient database records, wherein the machine-learning model is configured to determine a respective confidence indicator associated with the classified EGM dataset of each of the patient database records and is indicative of a degree of confidence relating to the IMD classification and the EGM segment data of the classified EGM dataset. The instructions further cause the one or more processors 802c to identify in the data processing system 350, 800, at least one patient database record for display and provide for display on a display device 307, 810 in communication with the data processing system 350, 800, the at least one patient database record identified for display.

FIG. 9 illustrates another form of system level diagram indicating potential devices and networks that utilize the methods and systems herein. For example, an IMD 902 may be utilized to collect a classified EGM dataset. The IMD 902 may supply classified EGM datasets, as well as sensitivity levels and motion data, to various local external devices, such as a tablet device 904, a smart phone 907, a bedside monitoring device 908, a smart watch and the like. Devices

904-908 each includes a display that may be configured to present the various types of the EGM signals/datasets, DD markers, statistics (e.g., % valid, % invalid), diagnostics, recommendations for adjustments in IMD sensing/therapy parameters and other information described herein. The IMD 902 may convey the classified EGM dataset over various types of wireless communications links to the devices 904, 907 and 908. The IMD 902 may utilize various communications protocols and be activated in various manners, such as through a Bluetooth, Bluetooth low energy, Wi-Fi or other wireless protocol. Additionally, or alternatively, when a magnetic device 910 is held next to the patient, the magnetic field from the device 910 may activate the IMD 902 to transmit the classified EGM dataset and arrhythmia data to one or more of the devices 904-908.

Embodiments may be implemented in connection with one or more IMDs. Non-limiting examples of IMDs include one or more of implantable leadless monitoring and/or therapy devices, and/or alternative IMD. For example, the IMD may represent a cardiac monitoring device (e.g., ICM), pacemaker, cardioverter, cardiac rhythm management device, defibrillator, leadless monitoring device, leadless pacemaker and the like. For example, the IMD may be a leadless implantable medical device (LIMD) that include one or more structural and/or functional aspects of the device(s) described in U.S. Pat. Nos. 9,216,285 and 8,831, 747, each of which is hereby incorporated by reference in its entirety. Additionally, or alternatively, the IMD may include one or more structural and/or functional aspects of the device(s) described in U.S. Pat. Nos. 8,391,980 and 9,232, 485, each of which is hereby incorporated by reference in its entirety. Additionally or alternatively, the IMD may be a subcutaneous IMD that includes one or more structural and/or functional aspects of the device(s) described in U.S. Pat. Nos. 10,765,860 B2, 10,722,704 B2, and 11,045,643 B2, each of which is hereby incorporated by reference in its entirety. Additionally or alternatively, the IMD may be a leadless cardiac monitor (ICM) that includes one or more structural and/or functional aspects of the device(s) described in U.S. Pat. Nos. 9,949,660 B2, 10,729,346 B2, 11,020,036 B2, 10,874,322 B2, and 10,777,880 B2, and in U.S. Patent Publication Nos. US20190336083A1 and US20210020294A1, each of which are hereby incorporated by reference in its entirety. Further, one or more combinations of IMDs may be utilized from the above incorporated patents and patent applications in accordance with embodiments herein.

Advantages of the Systems and Methods

Where the EGM segment data and respective classification data is initially obtained by an ICM, the ICM may be used for diagnostic purposes, e.g., to identify whether a patient experiences arrhythmic episodes, and if so, what types of arrhythmic episodes. More specifically, the ICM can collect a plurality of EGM segment data and associated IMD classification data for a period of time (e.g., one month), and such data can then be uploaded to a non-implanted system of a patient care network. Conventionally, a clinician would then review all of the EGM segments to confirm or reject the arrhythmia classifications determined by the ICM, and based thereon, the clinician can determine whether the patient should have a pacemaker implanted, be prescribed certain medication, have a certain medical procedure performed, and/or the like. However, as mentioned above, it is quite burdensome for a clinician to review all EGM segments that have been uploaded from an ICM or other type of IMD. Embodiments of the present technology, including those just summarized above, can be used to reduce the unnecessary EGM review burden imposed on ICM- or other IMD-implanted patients, while minimizing any delay-to-diagnosis.

For example, such embodiments can be used to reduce the number of EGM segments that a clinician needs to review per time period (e.g., per day) for each type of arrhythmic episode from potentially dozens per day, to just a few per day, while still enabling the clinician to identify a true positive arrhythmia detection on the first day such data was collected by an ICM. By reducing the number of EGM segments that need to be manually reviewed by a clinician, per type of arrhythmia, to only a few, clinically relevant EGM segments per day (or other time period) using one or more of the embodiments summarized above can substantially minimize delay in diagnosing patients as having a true positive arrhythmic episode.

It is a well understood problem that ICM devices generate a glut of inaccurate data that requires clinics to invest more time than desired in data management solutions. The systems and methods of the present disclosure offer improvements over the prior art by (a) storing the IMD recordings and IMD classifications for detected arrhythmic episodes in a plurality of classified EGM datasets on a remote server system (or other external device/system), (b) applying one or more machine-learning models to rank those remotely stored classified EGM datasets, according to a respective degree of confidence (as determined by the machine-learning model) for each IMD classification, (c) selecting for display only those records that ranked highest for respective degree of confidence, (d) performing additional processing to generate machine-adjudicated datasets to be used to generate diagnostic information, such as removing or re-classifying false positives, and/or interpolating missing data from the IMD recordings, thereby eliminating (or mitigating) errors that may be introduced by incorporating inaccurate data from classified EGM datasets containing, for example, false positives and/or missing temporal data.

A server-side solution of the present system and method further provides improved accuracy (leveraging an increase in computation capability over that of an IMD). As described herein, in some embodiments, one or more components of the system implement an alert to initiate EGM data transmissions from the IMD to the server system when the IMD is reaching capacity; the server system receives the EGM data and processes it by applying ML models and subsequent processing steps, as described herein, and then stores the results of such processing into a database of patient database records for the IMD-implanted patient. The database may be, for example, a longitudinal database. In such embodiments, classified EGM datasets, post-processing, are considered machine-adjudicated EGM datasets, which are used by the server system to generate patient diagnostic information for the clinician and to update patient alerts for the IMD, rather than the original, classified EGM datasets. For simplicity and compatibility with known clinical system architectures (e.g., merlin.net), the server provides patient database records, comprising machine-adjudicated EGM datasets, and diagnostic information relating thereto, in a format made compatible with known clinical systems architecture, such as e.g., Merlin.net™ Patient Care Network (Abbott) and MN5000.

More specifically, the systems and methods of the present disclosure describe how various patient-specific parameter settings may be used to configure and/or reprogram an IMD and set personalized display criteria for ML-adjudicated EGM datasets. In particular, and as described in detail above, ML-adjudicated datasets that are false may be hidden from the end user and not presented at all. In addition, the systems and methods enable clinical scenarios in which patient-specific settings for the IMD may be adjusted and/or (re)configured depending upon the stage of the patient's medical journey. For example, if a patient with unknown AF status has AF yet to be detected, IMD parameters can be set to high sensitivity with more false positive prediction to speed up the diagnosis. Once diagnosed, the patient will receive treatment—for example, (1) an interventional procedure like AF ablation, after which the patient's IMD may be set to an AF detection, or (2) AF management, where the patient may be asked to take oral anti-coagulant medications and/or rate control medications (e.g., beta blockers, etc.) as needed, in which case the patient need not be actively monitored for each AF episode, but only for when the condition deteriorates beyond the current baseline. Thus, one significant benefit of the systems and methods described herein lies in the ability to enable a clinician user to actively adjust parameters and other aspects of the diagnosis and monitoring system, according to the status of a patient's medical journey, thereby personalizing and simplifying patient management.

Additionally, and more specifically, clinical alert conditions relating to patient-specific longitudinal datasets that are created, modified and acted upon by the systems and methods of the present disclosure may also be assessed from diagnostic information thereby generated, and such clinical alert conditions may be conditionally reset, based upon such assessment. For example, in a case where the IMD is an ICM, AF burden may be associated with a defined clinical alert condition that depends on using the system's generated diagnostic information and/or ML-adjudicated datasets to create a new burden, upon which the alert detection algorithm including such new burden may be applied on the remaining arrhythmic episodes. Other clinical alerts can be related to the time of day, i.e., brady episodes at night-time (non-symptomatic), where alerts at night-time, even if considered true positives by the ML model, can be excluded based on the history of evaluation by the clinic and an input indicating that these night-time episodes are non-actionable. The logic to trigger clinical alerts in the present system is thus not limited to IMD firmware-rather, alerts may be triggered by new available data (e.g., diagnostic information and/or ML-adjudicated EGM datasets) generated by the system, and may be configured to respond when new data and/or information is uploaded from the IMD to the external system and certain defined conditions are met. Such alerts may be triggered upon arrival of new data, even if a previously defined trigger has not been modified as a clinical alert condition that persists in the new data.

Systems and methods for analyzing data obtained from an IMD using machine-learning architecture, and for managing alerts and diagnostics relating to such data are described herein. One such method includes receiving, in a data processing system (such as, for example, a cloud-based server system comprising one or more servers), classified EGM datasets corresponding to arrhythmic episodes detected by the IMD during a period of time, where each classified EGM dataset includes (1) EGM segment data corresponding to an arrhythmic episode, and (2) an IMD classification for the arrhythmic episode. In this embodiment, the classified EGM datasets are stored in a database of the server system. The server system processes this data by: (a) applying a machine-learning model to each classified EGM dataset (as stored in a patient database record), where the machine-learning model is configured to determine a respective confidence indicator indicative of a degree of confidence relating to the IMD classification of the classified EGM dataset; (b) updating the patient database record so as to include the respective confidence indicator so determined; (c) assigning a ranking score to the patient database record (comprising one classified EGM dataset), based upon the respective confidence indicator included in the patient database record, and in comparison to a set of other respective confidence indicators relating to the same type of arrhythmic episode and included in other ones of the patient database records of the database; (d) identifying, based upon the ranking scores so assigned, at least one patient database record for display; and (e) providing for display (on a display device in communication with the data processing system) such patient database record(s) identified for display. Other embodiments of this aspect include corresponding computer systems, apparatus, and computer programs recorded on one or more computer storage devices, each configured to perform the actions of the method described above.

For example, in some embodiments, a data processing system to perform the methods described herein may include (a) an IMD configured to detect, record and transmit a plurality of signals corresponding to classified EGM datasets representing a set of arrhythmic episodes; (b) an external device configured to receive and re-transmit said plurality of signals to (c) a server system informationally connected (aka communicatively coupled) to the external device via a communication link. In such embodiments, the server system may include one or more server processors, a database, a server memory, and a network interface, where such server components collectively operate to: (a) store and execute (on one or more processors) a machine-learning model configured to determine at least one confidence indicator relating to each classified EGM dataset in the plurality of classified EGM datasets, and to generate, for each classified EGM dataset, a machine-adjudicated EGM dataset including the at least one confidence indicator; (b) store and execute (on one or more processors) a second set of instructions configured to generate a set of diagnostic information and/or alerts based upon a plurality of said machine-adjudicated EGM datasets; (c) store and execute (one on or more processors) a third set of instructions configured to select for display at least one machine-adjudicated EGM dataset from the plurality of said machine-adjudicated EGM datasets; and/or (d) store in the database the plurality of machine-adjudicated EGM datasets in relation to the set of arrhythmic episodes and the set of diagnostic information. The server system is further configured to transmit signals representing the subset of machine-adjudicated EGM datasets to a clinician's display device informationally connected (aka communicatively coupled) to the server system.

In some embodiments, an external storage and processing system of the present disclosure is more specifically configured to: (a) receive, from a remote device, a plurality of classified EGM datasets, where each classified EGM dataset includes EGM segment data and an associated classification, where the EGM segment data represents an arrhythmic episode detected by an IMD during a period of time; (b) store, in a longitudinal database, the plurality of classified EGM datasets; (c) process the plurality of classified EGM datasets using a machine-learning model to (1) determine a set of true positive arrhythmic episodes detected by the IMD and generate a first set of identifying information (such as, e.g., confidence indicators, date/time stamps, and/or DD markers) relating to the set of true positive arrhythmic episodes, and (2) determine a set of false positive arrhythmic episodes detected by the IMD and generate a second set of identifying information relating to the set of false positive arrhythmic episodes; (d) rank the set of true positive arrhythmic episodes based upon the first set of identifying information, to obtain a ranking score for each classified EGM dataset corresponding to a true positive arrhythmic episodes; updating the longitudinal database to include the identifying information relating to the true positive arrhythmic episode(s) and the ranking score corresponding to each such true positive arrhythmic episode; (e) remove, from the longitudinal database, each classified EGM dataset from the plurality of classified EGM datasets corresponding to a false positive arrhythmic episode, based upon the second set of identifying information relating to the false positive arrhythmic episode(s), thereby obtaining a plurality of machine-adjudicated EGM datasets from the plurality of classified EGM datasets; (f) generate a set of diagnostic information based upon the machine-adjudicated EGM datasets; (g) select for display a subset of the machine-adjudicated EGM datasets, based upon their ranking scores and identifying information (relating to each true positive arrhythmic episode); and (h) provide for display on a display device in communication with the system, the set of diagnostic information and the subset of machine-adjudicated EGM datasets comprising EGM segment data to be displayed. Other embodiments of this aspect include corresponding computer systems, apparatus, and computer programs recorded on one or more computer storage devices, each configured to perform the actions of the methods.

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase®, SAS® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random-access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the embodiments of the present technology as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the embodiments of the present technology to the specific form or forms disclosed, but on the contrary, the intention is to cover all modifications, alternative constructions and equivalents falling within the spirit and scope of the embodiments of the present technology, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and physical characteristics described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claim is:

1. A method for analyzing data obtained from an implantable medical device (IMD), the method comprising:

receiving, in a data processing system, a plurality of classified electrogram (EGM) datasets corresponding to a plurality of arrhythmic episodes detected by the IMD during a period of time, wherein each classified EGM dataset comprises EGM segment data corresponding to one of the arrhythmic episodes and an IMD classification for the arrhythmic episode;

storing the plurality of classified EGM datasets in a respective plurality of patient database records of a database;

applying, in the data processing system, a machine-learning model to each classified EGM dataset of the plurality of patient database records, wherein the machine-learning model is configured to determine a respective confidence indicator associated with the classified EGM dataset of each of the patient database records and a degree of confidence relating to the IMD classification and the EGM segment data of the classified EGM dataset;

identifying, in the data processing system, at least one patient database record for display; and providing for display on a display device in communication with the data processing system, the at least one patient database record identified for display.

2. The method of claim 1, wherein the database comprises a longitudinal database.

3. The method of claim 1, further comprising for each of at least two or more of the plurality of patient database records of the database:

updating, in the data processing system, the patient database record so as to include the respective confidence indicator determined for and associated with the classified EGM dataset stored in the patient database record; and assigning, in the data processing system, a ranking score to the patient database record based upon the respective confidence indicator included in the patient database record, and in comparison to a set of respective confidence indicators relating to a same type of arrhythmic episode and included in other ones of the patient database records stored in the database; and wherein the identifying, in the data processing system, the at least one patient database record for display, is based upon the ranking scores assigned to the plurality of patient database records.

4. The method of claim 1, wherein for each classified EGM dataset, the respective confidence indicator is indicative of a degree of confidence of at least one of the following:

that the IMD classification included in the classified EGM dataset represents a true positive designation of a type of arrhythmic episode corresponding to the EGM segment;

that the IMD classification included in the classified EGM dataset represents a false positive designation of a type of arrhythmic episode corresponding to the EGM segment;

in an accuracy of identifying an EGM signal feature of a type of arrhythmic episode;

in a sensitivity level utilized by the IMD to identify one or more EGM signal features corresponding to a type of arrhythmic episode; or a degree of signal noise in the EGM segment data of the classified EGM dataset.

5. The method of claim 1, further comprising:

determining whether the plurality of classified EGM datasets corresponding to the plurality of arrhythmic episodes detected by the IMD during the period of time includes a data signal temporal gap corresponding to missing information in the plurality of classified EGM datasets;

interpolating an approximate EGM dataset suggested by the data signal temporal gap;

storing the approximate EGM dataset in the database; and generating diagnostic information from at least one of the patient database records and the approximate EGM dataset.

6. The method of claim 1, further comprising:

determining an alternative classification for one or more said classified EGM dataset stored in the plurality of patient database records for which the respective confidence indicator associated with the classified EGM dataset is indicative of a false positive designation of a type of arrhythmic episode corresponding to the EGM segment data; and modifying one or more said patient database record for which the respective confidence indicator associated with the classified EGM dataset is indicative of a false positive designation of the type of arrhythmic episode by replacing the IMD classification with the alternative classification and by updating the respective confidence indicator to an alternative confidence indicator, thereby associating a different type of arrhythmic episode with the EGM segment data of the classified EGM dataset stored in the patient database record.

7. The method of claim 1, further comprising:

facilitating a reprogramming of a set of instructions stored in the IMD in response to a plurality of said respective confidence indicators indicating a threshold level alert for at least one type of arrhythmic episode of the plurality of arrhythmic episodes detected by the IMD during the period of time.

8. The method of claim 1, further comprising:

removing one or more said patient database record from the database for which the respective confidence indicator included in the patient database record is indicative of a false positive designation of the type of arrhythmic episode corresponding to the EGM segment data of the patient database record, thereby creating a plurality of machine-adjudicated patient database records stored in the database;

generating diagnostic information from at least some of the machine-adjudicated patient database records; and providing for display on the display device the diagnostic information.

9. The method of claim 8, wherein:

the generating the diagnostic information includes associating a diagnostic alert with at least one type of arrhythmic episode represented in the plurality of arrhythmic episodes, based upon one or more confidence indicators of a plurality of said respective confidence indicators.

10. The method of claim 9, wherein:

the associating the diagnostic alert with the at least one type of arrhythmic episode is further based upon the diagnostic information.

11. A data processing system for analyzing a dataset associated with electrogram (EGM) data, the data processing system comprising:

an implantable medical device (IMD) configured to detect, record and transmit a plurality of signals corresponding to a plurality of classified EGM datasets representing a set of arrhythmic episodes;

an external device configured to receive the plurality of signals from the IMD and to re-transmit the plurality of signals over a communication link; and a server system informationally connected to the external device via the communication link, the server system comprising one or more server processors, a database, a server memory, and a network interface;

wherein the server memory is configured to store (1) a first set of instructions corresponding to a machine-learning model configured to determine at least one confidence indicator relating to each classified EGM dataset in the plurality of classified EGM datasets, and to generate, for each classified EGM dataset, a machine-adjudicated EGM dataset including the at least one confidence indicator, (2) a second set of instructions configured to generate a set of diagnostic information based upon a plurality of said machine-adjudicated EGM datasets generated by the machine-learning model, and (3) a third set of instructions configured to select for display at least one machine-adjudicated EGM dataset from the plurality of said machine-adjudicated EGM datasets;

wherein the one or more server processors are configured to (a) execute the first set of instructions to determine the at least one confidence indicator for each classified EGM dataset and to generate each machine-adjudicated EGM dataset in the plurality of said machine-adjudicated EGM datasets, and (b) execute the second set of instructions to generate the set of diagnostic information based upon the plurality of said machine-adjudicated EGM datasets, and (c) execute the third set of instructions to select for display a subset of machine-adjudicated EGM datasets from the plurality of said machine-adjudicated EGM datasets;

wherein the database is configured to store the plurality of said machine-adjudicated EGM datasets in relation to the set of arrhythmic episodes and the set of diagnostic information; and wherein the network interface is configured to transmit signals representing the subset of machine-adjudicated EGM datasets to a display device informationally connected to the network interface.

12. The data processing system of claim 11, wherein:

the server system is a cloud-based system, and the communication link is a wireless communication link.

13. The data processing system of claim 11, wherein:

the IMD is further configured to transmit an alert signifying a request to initiate transmission of the plurality of signals to the external device.

14. The data processing system of claim 11, further comprising:

a data storage configured to save the plurality of classified EGM datasets, each classified EGM dataset representing an arrhythmic episode in the set of arrhythmic episodes;

wherein the second set of instructions is configured to identify a temporal gap in the plurality of classified EGM datasets, interpolate an approximate EGM dataset suggested by the plurality of classified EGM datasets, and update the data storage to include the approximate EGM dataset along with the plurality of classified EGM datasets so as to mitigate error associated with the temporal gap.

15. The data processing system of claim 14, wherein the data storage is a component of the database.

16. The data processing system of claim 14, wherein the database is a longitudinal database.

17. A system comprising a memory storing a set of instructions, and one or more processors configured to execute the set of instructions to perform:

receiving, from a remote device, a plurality of classified electrogram (EGM) datasets, each classified EGM dataset comprising EGM segment data and an associated classification, and where the EGM segment data represents an arrhythmic episode detected by an implantable medical device (IMD) during a period of time;

storing, in a longitudinal database, the plurality of classified EGM datasets;

processing the plurality of classified EGM datasets using a machine-learning model to (a) determine a set of true positive arrhythmic episodes detected by the IMD and generate a first set of identifying information relating to the set of true positive arrhythmic episodes, and (b) determine a set of false positive arrhythmic episodes detected by the IMD and generate a second set of identifying information relating to the set of false positive arrhythmic episodes;

ranking the set of true positive arrhythmic episodes based upon the first set of identifying information, to obtain a ranking score for each classified EGM dataset corresponding to a member in the set of true positive arrhythmic episodes;

updating the longitudinal database to include the first set of identifying information relating to the set of true positive arrhythmic episodes and the ranking score for each classified EGM dataset corresponding to said member in the set of true positive arrhythmic episodes;

removing, from the longitudinal database, each classified EGM dataset from the plurality of classified EGM datasets corresponding to a member in the set of false positive arrhythmic episodes, based upon the second set of identifying information relating to the set of false positive arrhythmic episodes, thereby obtain a plurality of machine-adjudicated EGM datasets from the plurality of classified EGM datasets;

generating a set of diagnostic information based upon the plurality of machine-adjudicated EGM datasets;

selecting for display a subset of the machine-adjudicated EGM datasets, based upon a plurality of said ranking scores and the first set of identifying information relating to the set of true positive arrhythmic episodes; and providing for display on a display device in communication with the system, the set of diagnostic information and the subset of machine-adjudicated EGM datasets comprising EGM segment data to be displayed.

18. The system of claim 17, wherein:

the second set of identifying information relating to the set of false positive arrhythmic episodes comprises an input into an external system configured to remotely program the IMD.

19. The system of claim 17, wherein the processor is further configured to execute the set of instructions to perform:

generating a query to obtain a set of patient-specific parameter settings configured to (a) enable the machine-learning model to process a set of patient-specific longitudinal data relating to the set of arrhythmic episodes, and (b) select the set of diagnostic information and a set of display criteria associated with the subset of machine-adjudicated EGM datasets to be displayed.

20. The system of claim 19, wherein the processor is further configured to execute the set of instructions to perform:

generating a second query to obtain a set of alert conditions relating to the set of arrhythmic episodes and the patient-specific longitudinal data;

generating at least one assessment of an alert condition of the set of alert conditions based upon the set of diagnostic information; and conditionally resetting the set of alert conditions based upon the at least one assessment.

21. The system of claim 17, wherein:

the set of patient-specific parameters settings includes a configurable time period used to generate the set of diagnostic information.

22. The system of claim 17, wherein the set of instructions to perform processing the plurality of classified EGM datasets using the machine-learning model includes a subset of instructions to perform:

identifying a temporal gap in the plurality of classified EGM datasets corresponding to missing information;

interpolating an approximate EGM dataset suggested by the temporal gap; and storing the approximate EGM dataset in the longitudinal database so as to mitigate error associated with the temporal gap.

* * * * *